(12) United States Patent
Bockeria

(10) Patent No.: US 11,103,710 B2
(45) Date of Patent: Aug. 31, 2021

(54) SYSTEMS, METHODS, AND DEVICES FOR TREATING BRADYARRHYTHMIAS, TACHYARRHYTHMIAS AND HEART FAILURE

(71) Applicants: Olga Bockeria, Berwyn, PA (US); Roseanne Satz, Lake Worth, FL (US)

(72) Inventor: Olga Bockeria, Moscow (RU)

(73) Assignees: Olga Bockeria, Berwyn, PA (US); Roseanne Satz, Lake Worth, FL (US)

( * ) Notice: Subject to any disclaimer, the term of this patent is extended or adjusted under 35 U.S.C. 154(b) by 228 days.

(21) Appl. No.: 16/430,330

(22) Filed: Jun. 3, 2019

(65) Prior Publication Data
US 2019/0366098 A1  Dec. 5, 2019

Related U.S. Application Data

(60) Provisional application No. 62/679,958, filed on Jun. 3, 2018.

(51) Int. Cl.
*A61N 1/05* (2006.01)
*A61N 1/368* (2006.01)
(Continued)

(52) U.S. Cl.
CPC ....... *A61N 1/36843* (2017.08); *A61N 1/0587* (2013.01); *A61N 1/3756* (2013.01);
(Continued)

(58) Field of Classification Search
CPC ...... A61N 1/0587; A61N 1/059; A61N 1/362; A61N 1/3621; A61N 1/3622;
(Continued)

(56) References Cited

U.S. PATENT DOCUMENTS 4,157,720 A * 6/1979 Greatbatch ............ A61N 1/375
607/131
4,256,115 A * 3/1981 Bilitch ................. A61N 1/0587
607/135
(Continued)

FOREIGN PATENT DOCUMENTS

CN 202777464 3/2013
EP 036866 A2 4/1998
(Continued)

OTHER PUBLICATIONS

Bockeria, Olga. Curriculum vitae. <http://bakulev.academia.edu/OlgaBockeria/CurriculumVitae> Jan. 20, 2018. Accessed Aug. 2, 2019.*
(Continued)

*Primary Examiner* — Eugene T Wu
(74) *Attorney, Agent, or Firm* — Bonini IP Law, LLC; Frank J. Bonini, Jr.

(57) ABSTRACT

A method, system and device for monitoring and treating conditions of a mammalian heart, among which may include bradyarrhythmias, tachyarrhythmias and heart failure, the device being configured as a pacemaker that harvests energy as it implements the pacemaker functions to treat and monitor conditions of the heart. The pacemaker has a case, electrical circuitry sealed within the case, an electrode that is electrically coupled to the electrical circuitry, and embodiments may include a microelectromechanical system (MEMS) for harvesting and converting the kinematic energy of the heart into electrical energy. Embodiments provide receivers at locations of the heart which sense heart activity and are controlled with pacing circuitry to deliver electrical impulses at locations and time intervals to replicate the contractions of a normal functioning heart. Further embodiments provide a multi-part pacemaker where case-connect-
(Continued)

able electrode part may be implanted separately from the case part.

20 Claims, 15 Drawing Sheets

(51) Int. Cl.
  *A61N 1/372* (2006.01)
  *A61N 1/378* (2006.01)
  *A61N 1/375* (2006.01)
(52) U.S. Cl.
  CPC ....... *A61N 1/3785* (2013.01); *A61N 1/37205* (2013.01); *A61N 1/37223* (2013.01)
(58) Field of Classification Search
  CPC .... A61N 1/3627; A61N 1/368; A61N 1/3684; A61N 1/36842; A61N 1/36843; A61N 1/372; A61N 1/37205; A61N 1/375; A61N 1/37512; A61N 1/3756; A61N 1/378; A61N 1/3785; A61N 1/3787
  See application file for complete search history.

(56) References Cited

U.S. PATENT DOCUMENTS

| | | | |
|---|---|---|---|
| 4,289,929 A | | 9/1981 | Hathaway |
| 4,928,690 A * | | 5/1990 | Heilman .............. A61B 5/6831 600/509 |
| 5,902,324 A * | | 5/1999 | Thompson ........... A61N 1/3627 607/9 |
| 6,141,588 A * | | 10/2000 | Cox ..................... A61N 1/3622 128/903 |
| 6,584,352 B2 | | 6/2003 | Combs et al. |
| 6,654,638 B1 | | 11/2003 | Sweeney |
| 7,092,751 B2 | | 8/2006 | Erkkilä |
| 7,283,874 B2 | | 10/2007 | Penner |
| 7,498,681 B1 | | 3/2009 | Kellogg et al. |
| 7,787,951 B1 | | 8/2010 | Min |
| 8,364,276 B2 | | 1/2013 | Willis |
| 8,527,068 B2 | | 9/2013 | Ostroff |
| 8,795,150 B2 | | 8/2014 | Forsell |
| 9,149,641 B2 | | 10/2015 | Stahmann et al. |
| 9,155,479 B2 | | 10/2015 | Solem |
| 9,259,580 B2 | | 2/2016 | Brenner et al. |
| 9,333,364 B2 | | 5/2016 | Echt et al. |
| 9,393,436 B2 | | 7/2016 | Doerr |
| 9,409,033 B2 | | 8/2016 | Jacobson |
| 9,498,130 B2 | | 11/2016 | Najafi et al. |
| 9,597,514 B2 | | 3/2017 | Khairkhahan et al. |
| 9,616,242 B2 | | 4/2017 | Imran |
| 9,814,896 B2 | | 11/2017 | Solem |
| 9,907,968 B2 | | 3/2018 | Moore et al. |
| 9,999,713 B2 | | 6/2018 | Solem |
| 2005/0055061 A1 | | 3/2005 | Holzer |
| 2006/0085041 A1 * | | 4/2006 | Hastings .............. A61N 1/0587 607/33 |
| 2009/0171408 A1 | | 7/2009 | Solem |
| 2009/0204170 A1 * | | 8/2009 | Hastings .............. A61N 1/3756 607/33 |
| 2011/0270339 A1 | | 11/2011 | Murray, III et al. |
| 2011/0270340 A1 | | 11/2011 | Pellegrini et al. |
| 2011/0276102 A1 | | 11/2011 | Cohen |
| 2012/0116489 A1 * | | 5/2012 | Khairkhahan ......... A61N 1/375 607/127 |
| 2012/0150252 A1 | | 6/2012 | Feldman et al. |
| 2012/0330392 A1 * | | 12/2012 | Regnier ................ A61N 1/059 607/119 |
| 2013/0238073 A1 | | 9/2013 | Makdissi et al. |
| 2015/0088155 A1 | | 3/2015 | Stahmann et al. |
| 2015/0088221 A1 | | 3/2015 | Yaniv-Barr-Cohen |
| 2016/0030757 A1 * | | 2/2016 | Jacobson ............... A61N 1/372 607/4 |
| 2016/0051811 A1 * | | 2/2016 | Doerr ................... A61B 17/064 606/191 |
| 2016/0346556 A1 | | 12/2016 | Slepian et al. |
| 2017/0077839 A1 | | 3/2017 | Karami et al. |
| 2017/0197085 A1 | | 7/2017 | Imran |
| 2018/0008829 A1 | | 1/2018 | An et al. |
| 2018/0056079 A1 | | 3/2018 | Hahn et al. |

FOREIGN PATENT DOCUMENTS

| | | | |
|---|---|---|---|
| RU | 143968 U1 * | 8/2014 | |
| RU | 174283 U1 | 10/2017 | |
| WO | 9317154 | 9/1993 | |
| WO | 2004073138 | 11/2005 | |
| WO | 2013074419 | 5/2013 | |
| WO | 2013152259 | 2/2015 | |

OTHER PUBLICATIONS

Machine translation of RU 143968 U1. Accessed Aug. 2, 2019.*
Bockeria et al. "A leadless epicardial pacemaker". EP Europace, vol. 19, Issue suppl_3, Jun. 2017, p. iii389.*
Bockeria et al. "Potential Use of Heart Contractions as a Source of Energy for Implantable Devices". Biomedical Engineering, vol. 52, No. 6, Mar. 2019, pp. 412415. Translated from Meditsinskaya Tekhnika, vol. 52, No. 6, Nov. Dec. 2018, pp. 3638.*
Ning, Li et al., "Direct Powering a Real Cardiac Pacemaker by Natural Energy of a Heartbeat," article, Jan. 24, 2019, ACS NANO, Shanghai, China.
Turley, Andrew, "Introduction to Cardiac Device Function and Trouble Shooting," digital presentation, Heart Rhythm UK.
Geisinger, "Permanent His Bundle Pacing Is Associated with Reduction in Morbidity and Mortality Compared to Right Ventricular Pacing," presentation, Journal of the American College of Cardiology, USA, (2018) doi: 10.1016/ j.jacc.2018.02.048.
www.ebrsystemsinc.com, 2019, EBR Systems Inc.
Kenneth A. Ellenbogen, Pugazhendhi, Vijayaraman, "His Bundle Pacing a New Promise in Heart Failure Therapy?" journal, 2015, vol. 1, No. 6, Journal of the American College of Cardiology: Clinical Electrophysiology, Elsevier, Inc., USA.
Venkateswara Sarma Mallela, V. Ilankumaran, N.Srinivasa Rao, "Trends in Cardiac Pacemaker Batteries," journal, 2004, 201-212, vol. 4, No. 4, Indian Pacing and Electrophysiology Journal.
Brian Olshansky, Jeffrey N Rottman,"Pacemaker-Mediated Tachycardia Treatment & Management," article, Aug. 4, 2016, Medscape.
Chu-Pak Lau, "The Range of Sensors and Algorithms Used in Rate Adaptive Cardiac Pacing, "Aug. 1992, 1177-1211, vol. 15, Pace, Hong Kong, China.
Chu-Pak Lau, Hunf-Fat Tse, A. John Camm, Serge S. Barold, "Evolution of pacing for bradycardias: sensors," journal, 2007, I11-I22, vol. 9, European Heart Journal Supplements.
Achraf Ben Amar, Ammar B. Kouki, Hung Cao, "Power Approaches for Implantable Medical Devices," journal, Nov. 13, 2015, 28889-28914, vol. 15, Sensors.
Sertac Haydin, Murat Saygi, Yakup Ergul, Isa Ozyilmaz, Erkut Ozturk, Celal Akdeniz, Volkan Tuzcu, "Subxiphoid Approach to Epicardial Implantation of Implantable Cardioverter Defibrillators in Children," journal, 2013, 1-5, vol. 00, Pace, Wiley Periodicals, Inc.
Costa et al., "Minimally Invasive Epicardial Pacemaker Implantation in Neonates with Congenital Heart Block," journal, 2017, 331-339, vol. 109, No. 4, Arq Bras Cardiol.
Sperzel et al., "State of the art of leadless pacing," journal, May 29, 2015. 1508-1513, vol. 17, European Society of Cardiology, Europace, Oxford University Press.

* cited by examiner

SYSTEMS, METHODS, AND DEVICES FOR TREATING BRADYARRHYTHMIAS, TACHYARRHYTHMIAS AND HEART FAILURE

CROSS-REFERENCE TO RELATED APPLICATION

This application claims the benefit to U.S. Provisional Application 62/679,958 filed on Jun. 3, 2018, the entire contents of which are incorporated herein by reference

BACKGROUND OF THE INVENTION

1. Field of the Invention

The present invention relates to the field of cardiac medicine, and in particular, methods, systems and devices for cardiac treatment and monitoring of conditions of the heart, including monitoring and treating bradyarrhythmias, tachyarrhythmias and heart failure, and turning the kinematic energy of the heart into electrical energy for powering the operations of a pacemaker.

2. Brief Description of the Related Art

The heart is an organ of the body which moves blood throughout the body. As the heart beats, it provides pressure to move blood through a network of arteries, and veins that serve as the return path. The arterial flow of blood delivers oxygen and important nutrients to tissue throughout the human body. The heart has four chambers which pump the blood. The heart chambers include an upper and continuous lower chamber on each side of the heart. The heart's four chambers include the right atrium, which receives venous oxygen-depleted blood that has already circulated around through the body (not including the lungs). The blood is pumped from the right atrium to into the right ventricle. The right ventricle is a chamber that pumps blood from the right atrium to the pulmonary artery which carries the deoxygenated blood to the lungs. At the lungs the blood picks up oxygen in exchange for carbon dioxide. The left atrium is the chamber that receives oxygenated blood from the pulmonary veins of the lungs and pumps it to the left ventricle. The left ventricle is comprised of the thickest muscle mass of all the heart chambers. The left ventricle pumps blood to the heart and rest of the body (other than the lungs).

The two atria are located in the top of the heart and receive blood from the veins. The two ventricles are located in the bottom of the heart and pump blood into the arteries.

For the heart function, the atria and ventricles contract to make the heart beat and to pump the blood through each chamber. The heart chambers fill up with blood before each beat. The contraction of the atria and ventricles pushes blood out into the next chamber. The heart also has four valves. There is a valve at the downstream end of each chamber, which for a healthy heart, operating in a normal manner, restricts the flow so that blood does not flow backward. The valves therefore enable the chambers to fill with blood and pump blood forward in the normal operating manner.

The heart contractions are regulated by electrical impulses. These electrical impulses start from the autonomic sinus node (which also is referred to as the sinoatrial node, or SA node), which is located in the tissue of the right atrium. An electrophysiologic (EP) signal is generated by the SA node and spreads in the right and left atrium, causing them to contract. The electrical pulses or signal then travels through the heart to the atrioventricular node (AV node). The AV node is situated near the center of the heart, between the atria and the ventricles.

A healthy heart maintains a proper rhythm to keep blood flowing, and the electrical impulses are responsible for the rhythm.

The normal cardiac cycle includes contractions of the atrial muscles, which are activated by the autonomic sinoatrial node (SA node), also called the sinus node. The electrophysiologic (EP) signal generated by the SA node spreads in the right and left atrium leading to their contraction. The EP signal further reaches the atrioventricular node (AV node) situated between the atria and the ventricles. The AV node delays the EP signal, giving the atria time to contract completely before the ventricles are stimulated. After the delay in the AV node the EP signal spreads to the ventricles via the fibers of the His-Purkinje system leading to the contraction of the ventricles. After the contraction, the atria are relaxed and filled by blood coming from venous return. The entire cardiac cycle is the combination of atrial and ventricular contraction, i.e., depolarization, and their relaxation, i.e. repolarization.

The cardiac cycle may be measured. This is typically done through a non-invasive measurement that involves attaching small electrodes on the skin of the patient. The voltage differences caused by the heart between the electrodes are measured and recorded to generate an electrocardiogram (ECG) of the patient. The ECG measures the electrical activity of the heart and generates corresponding signals that represent waves. A cardiac cycle typically includes waves, where the P wave represents the systole of the atria, the QRS wave represents the systole of ventricles, and the T wave represents their repolarization. The heart rate is typically expressed in beats per minute (bpm). The heart rate of a healthy functioning heart in normal conditions may not be constant, and therefore, there is typically variation in the heart rate, commonly termed, heart rate variability or HRV. The atrial muscles contract from the superior portion of the atria toward the atrioventricular septum. As this occurs, pressure rises within the atria and blood is pumped into the ventricles through the open atrioventricular valves (i.e., the tricuspid valve between the right atrium and right ventricle, and the mitral or bicuspid valve between the left atrium and left ventricle). For a normal heart function in an adult, at the start of atrial systole, the ventricles typically contain approximately 70-80 percent of their filled capacity as a result of blood inflow during diastole. The remaining 20 to 30 percent of the filling takes place as a result of atrial contraction. Referring to FIG. 1, atrial systole ends prior to ventricular systole, taking place as the atrial muscle returns to diastole and lasting a duration of about 100 ms.

FIG. 1 also depicts the ventricular systole, which follows the depolarization of the ventricles. In FIG. 1, ventricular systole is represented by the QRS complex in the ECG. At the conclusion of atrial systole, immediately before the atrial contraction, the ventricles will contain (in a normal healthy adult) about 130 mL of blood, which is designated the end diastolic volume (EDV) or preload. The ventricles contract, and the pressure of blood within the ventricular chambers rises, but it is not yet forced out of the heart, since the pressure does not reach the threshold level to open the semilunar valves i.e., the pulmonary valve and aortic valve, and these valves close off the lower right chamber (or right ventricle), and lower left chamber (or left ventricle), respectively. When the pulmonary valve opens, it allows blood to be pumped from the heart to the lungs (through the pulmonary artery) where the blood will then receive oxygen. The aortic valve closes off the lower left chamber (the left ventricle) that holds the oxygen-rich blood before that blood is then pumped from the heart (via the aorta) to the body.

Upon the blood being ejected from the heart, blood pressure quickly rises above that of the atria, which are now relaxed and in diastole. As a result of the increase in pressure, blood flows back toward the atria, thereby closing the tricuspid and mitral valves. At this stage, the blood is not being ejected from the ventricles, and therefore, blood volume within the chamber remains constant. This is the initial stage of the ventricular systole and is generally termed isovolumetric contraction. The next or second stage of the ventricular systole is an ejection phase where the ventricular muscle contracts and raises the pressure within the ventricle. The raise of the ventricular pressure is therefore greater than the pressures in the pulmonary trunk and the aorta, and blood is pumped from the heart, pushing open the pulmonary and aortic semilunar valves. The pressure produced by the left ventricle is greater than the pressure produced by the right ventricle, but both ventricles pump the same amount of blood, the quantity of blood pumped being known as the stroke volume. A typical stroke for a healthy adult may be about 70-80 mL. Due to the commencement of the ventricular systole starting with an EDV of about 130 mL of blood, then after contraction there remains a fraction of blood in the ventricle, which is about 50-60 mL (which is the end systolic volume or ESV).

Following the repolarization of the ventricles, the heart undergoes ventricular diastole (which is ventricular relaxation). In FIG. 1, ventricular diastole is represented by the T wave of the ECG, and is divided into two distinct phases a first or early phase and a second phase. Ventricular diastole in a normal healthy heart may last about 430 ms. During the first or early phase of ventricular diastole, as the ventricular muscle relaxes, pressure on the remaining blood within the ventricle begins to fall. This phase is known as the isovolumetric ventricular relaxation phase. As a result of the pressure within the ventricles dropping below the pressure in both the pulmonary trunk and aorta, the blood flows back toward the heart. This produces what is known as the dicrotic notch, which is a small dip represented in blood pressure tracings. Backflow of blood into the heart is prevented as the semilunar valves close. The blood volume in the ventricle remains unchanged, as the atrioventricular valves remain closed. The second phase of ventricular diastole is often referred to as the late ventricular diastole. In this second phase the ventricular muscle relaxes, and pressure on the blood within the ventricles drops even further. The ventricular pressure eventually drops to a level below that of the atria, whereupon blood flows from the atria into the ventricles, pushing open the tricuspid and mitral valves.

The drop of pressure realized within the ventricles enables the blood to flow from the major veins into the relaxed atria, and from the atria into the ventricles. At this stage of the heart cycle, both chambers are in diastole, the atrioventricular valves are open, and the semilunar valves are closed.

One type of affliction affecting the heart is heart failure. Heart failure is a chronic, progressive condition. Typically, heart failure occurs because the heart muscle is unable to pump enough blood through to supply the body's needs for blood and oxygen. As a result, the heart cannot keep up with the demand put on it. The heart may attempt to make up for this by stretching so as to provide a greater thrust to the blood. But this stretching over time enlarges the heart. This enlargement or increase in muscle mass occurs because the contracting cells of the heart get bigger. Although the heart may pump more strongly, at least initially, the condition has additional negative effects. The heart also may pump faster to attempt to fulfill the body's demand. The body also may react to the heart's increased demand by blood vessel narrowing to keep blood pressure up (e.g., to try to make up for the heart's loss of power). Organs of the body may receive reduced blood flow owing to the diversion of blood flow to the heart and brain (where the heart is unable to meet the total demand). Blood flow may be diverted away from less important tissues and organs (like the kidneys). These remedies are temporary and may mask the problem of heart failure, and the responses of the body to attempt to alleviate the problem do not eradicate it. Heart failure continues and worsens until these substitute processes no longer work.

A cycle of an ECG signal is illustrated in FIG. 1, showing a typical one-cycle ECG tracing for a normal healthy heart. Modern ECG devices use digital signal processing to analyze the shape and the consistency of, and the durations between these waveforms. The depiction in FIG. 1 shows waves of the ECG signal, which represents the depolarization and repolarization events in the heart. These events are named alphabetically from P to U. In FIG. 1, the phase of each cardiac cycle is represented by the ECG signal, wherein the P wave represents the systole of the atria, the QRS wave represents the systole of ventricles, and T wave represents their repolarization. The ECG processes digital signals to analyze the waveforms, and determines the wave shape, consistency of the waves, and their duration. The PR interval is shown in FIG. 1, from the beginning of the P wave (the onset of atrial depolarization) until the beginning of the QRS complex (the onset of ventricular depolarization). The PR interval is the period and is measured in milliseconds. For a normal functioning heart, the PR interval typically is between 120 and 200 ms in duration. The PR segment is shown in FIG. 1 and represents the line segment that begins with the end of the P wave and ends with the beginning of the QRS. The PR segment corresponds to the period between the end of atrial depolarization and the onset of ventricular depolarization. The ST segment is shown in FIG. 1 corresponding to an isoelectric line after the QRS complex. The ST segment represents phase 2 of the cardiac action potential. For example, where the ECG exhibits elevation or depression of the ST segment, this may indicate myocardial ischemia or injury and coronary artery disease.

The heart rate (HR) which represents the number of beats per minute (bpm), may be measured by calculating the number of QRS waves in a minute. The rate of a heart functioning in a normal manner is not a constant. Heart rate variation (HRV) has become a widely used marker for indicating the cardiac condition of a patient.

The ECG signal is analyzed to detect conditions or disorders of the heart. The ECG analysis may detect abnormalities in the heart rhythm, commonly referred to as arrhythmias.

There are a number of abnormal cardiac rhythms. One type of abnormal cardiac rhythm is atrial fibrillation (AF). During AF, the atria lose the nominal control pattern induced by the SA node. Instead, the contraction might start randomly in other areas of the atria or even in the pulmonary veins. Unlike the normal functioning heart, in AF, the electrical current does not flow in an organized top-to-bottom fashion. Rather, contractions may be rapid and disorganized. For example, when a heart experiences a condition of AF, the AV node may not regulate the chaotic current. Although the AV node attempts to protect the ventricle from these extra electrical impulses, it is unable to stop all of them, and therefore, the ventricle beats more often than it normally should. This often leads to the symptoms of breathlessness and fatigue in the patient experiencing AF. When the beat is off, the atria and ventricles no longer beat in a coordinated way, since although the atria may be beating fast, the ventricles do not beat in the same fashion and they are no longer synchronized. Thus a fast and irregular heart rhythm is produced in the patient. For example, in AF, the ventricles may beat about 100 to 175 times a minute, in contrast to a normal rate of about 60 to 100 beats a minute. AF may produce contractions that commence simultaneously in different locations of the atria, and spreading therein. In AF, the P waves may even disappear from the ECG signal (see FIG. 1). Referring to the ECG in FIG. 1, AF is often detected by observing changes in the intervals between consecutive QRS complexes. AF may present dangers, which include the development of blood clots, which may remain circulating in the arteries, presenting the danger of making their way to organs, including the brain, to cause a stroke.

A bradyarrhythmia is another type of disorder, which occurs when the ventricular rate is less than 60 beats per minute (bpm). This disorder is generally the result of a dysfunction of the cardiac conduction system at the level of the sinus node, atria or the atrioventricular (AV) node. There are numerous causes that are considered responsible for bradyarrhythmias, among which include idiopathic fibrosis, infiltrative diseases, drugs, metabolic abnormalities, ischemic heart disease, traumatic injury and congenital heart diseases. Bradyarrhythmias may be determined based on the morphology of the P wave, the duration of the PR interval and the relation of the P wave to the QRS complex. An ECG may be used to obtain the data. Other testing is typically required to determine the type of bradyarrhythmia occurring, which in addition to ECG also may involve autonomic testing and electrophysiology study (EPS). In some instances, depending on the type of bradyarrhythmia determined, the bradyarrhythmia must be treated by implanting an electrical device known as a pacemaker.

There are different treatments for bradyarrhythmias, each of which depends on the type of electrical conduction problem, how severe a patient's symptoms are, and cause of the patient's slow heart rate. If the heart rate is slow, and there are no other symptoms, then the patient may be followed (with periodic check-ups), but no treatment may be required. In other instances, treatments for bradyarrhythmias may involve treating an underlying disorder that may be causing the bradyarrhythmia (e.g., such as hypothyroidism or obstructive sleep apnea). Often, when these disorders are properly treated, the bradyarrhythmia may resolve. Other causes of bradyarrhythmias are a number of medications, including some to treat other heart conditions. A bradyarrhythmia may be treated by changing medications or changing dosages of existing medications (e.g., a lower dose). However, where it is not possible to change or alter medications, and when resolving or treating underlying conditions fails to correct the bradyarrhythmia, then a pacemaker is necessary.

The pacemaker is a battery-operated device (currently about 1.5 to 3 inches, and about ¼ inch in thickness), which typically is implanted under a patient's skin to help regulate the heartbeat. Wires from the device known as leads, have electrodes at the end of the wires which are attached to heart tissues, or in other applications are placed within the chambers of the heart. The pacemaker monitors the patient's heart rate and generates electrical impulses as necessary to maintain an appropriate rate. A typical pacemaker has two parts, the leads (wires with electrodes at each end) and a pulse generator. The pulse generator houses a battery and includes a tiny computer. The pulse generator portion of the pacemaker is situated just under the skin of the patient's chest. In a typical implantation, the wire leads are threaded through the patient's veins into the heart, and implanted into the heart muscle. The leads conduct the electrical impulses from the pulse generator to the heart muscle, and, in addition, sense electrical activity of the heart. When the pacemaker is actuated to generate an impulse, the impulse causes the heart to contract. A pacemaker typically has one to three leads. There are three types of pacemakers, which include the single-chamber pacemakers which are deployed by placing one lead in the upper chamber (atria) or lower chamber (ventricles) of the right side of the heart. Another type is the dual-chamber pacemaker, which uses one lead in the right atrium, and one lead in the right ventricle. A third type of pacemaker is the biventricular pacemaker, which has three leads: one placed in the right atrium, one placed in the right ventricle, and one placed in the left ventricle (via the coronary sinus vein).

Pacemakers typically have a small computer that is programmed to generate the impulses. There are two main types of programming for pacemakers, which include demand pacing and rate-responsive pacing. Demand pacing is where the pacemaker monitors the patient's heart rhythm and only sends electrical pulses to the heart if the heart is beating too slow or if it misses a beat. Rate responsive pacing will speed up or slow down the patient's heart rate depending on patient activity. For example, the rate responsive pacemaker monitors factors, such as the patient's sinus node rate, breathing, and/or blood temperature, to determine the activity level.

A tachyarrhythmia (also referred to as a tachycardia) is another disorder of the heart rhythm characterized when a patient presents with a normal resting heart rate >100 bpm. There are a number of types of tachyarrhythmias. To differentiate tachyarrhythmias, they are classified as either narrow complex tachyarrhythmias (supraventricular tachycardias or tachyarrhythmias) or wide complex tachyarrhythmias (tachycardias). The designation of narrow and wide relate to the width of the QRS complex on an ECG. Narrow complex tachycardias/tachyarrhythmias tend to originate in the atria, while wide complex tachycardias/tachyarrhythmias tend to originate in the ventricles. Tachyarrhythmias may be further classified as either regular or irregular. Treatment and management of tachyarrhythmias depend on the type (i.e., wide complex versus narrow complex), whether or not the person is stable or unstable, and whether the instability is due to the tachyarrhythmia. In an unstable patient, the presence of a tachyarrhythmia may mean that organ functions are being affected, or that the person is likely to go into cardiac arrest.

Tachycardias may be diagnosed using cardiac imaging, which may include one or more of the following: echo cardiograms, magnetic resonance imaging (MRI), computerized tomography (CT), a coronary angiogram, and a chest x-ray. An echocardiogram uses sound waves to generate a moving picture of the heart, and in particular may identify areas of poor blood flow, abnormal heart valves, and improperly functioning heart muscle. The MRI may provide still or moving pictures of the blood flowing through the heart and detect irregularities. CT scans provide a detailed cross-sectional view of the heart by combining together several X-ray images. A coronary angiogram uses dye and x-rays to detect abnormalities or potential blockages, and provides information about the flow of blood through the heart and blood vessels and the inside of the coronary arteries. A chest x-ray may determine whether a patient's heart is enlarged. Treatments may include medication, as well as implantation of a small electrical device such as a pacemaker or cardioverter. Upon detection of an abnormal heartbeat, the pacemaker emits an electrical pulse that is delivered to the heart muscle to assist the heart to resume a normal beat. Another electrical device is an implantable cardioverter defibrillator (ICD).

Treatments for heart conditions have involved pacing of the right ventricle. However, RV pacing has been reported to lead to heart failure. In a reported study on the Geisinger His Bundle Pacing Registry data collected between 2013-2016, right ventricular pacing (RVP) was reported to be associated with heart failure and increased mortality. The Geisinger study looked at using His Bundle Pacing (HBP) as an alternative to RV pacing. The Geisinger study reported that permanent His Bundle Pacing (HBP) was found feasible and safe in a large, real-world population requiring permanent pacemakers. The Geisinger study reported that HBP was successful in 304 of 332 (92 percent) consecutive patients. Also included in the study were 433 patients who underwent RVP. The primary endpoint of death, heart failure hospitalization or upgrade to biventricular pacing was significantly reduced in the HBP group to 25 percent, compared to 32 percent of the RVP group (reporting that the difference being primarily in patients with ventricular pacing). In addition, the incidence of heart failure hospitalization was significantly reduced in HBP, 12.4 vs 17.6 percent, and a trend identified reduced mortality in HBP (17.2 vs. 21.4 percent). A normal heart has a shape of a cone, and there are three layers of muscle fibres within myocardium—longitudinal, circumferential and oblique. These layers contract simultaneously and this results in spiral contraction of the ventricles (primarily the left ventricle as it consists the 80% of the contraction part of the heart, with the ventricles reaching about 80% of their capacity before the atria begin to contract). The displacement of the heart, in a normally functioning heart, has 4 different variations and directions—radial displacement (mainly in the base of the heart, wherein the basic segments of the heart are usually work quite well even in heart failure), longitudinal—shortening of the axis (maximum on the apex), circumferential deformation, and torsion. Torsion happens first clockwise and, at the end of the systole, anticlockwise. This means that the movement starts from left to right (from LV to RV).

Now, when the right ventricle (RV) of the heart is paced, as it happens in VVI/R and/or DDD/R pacing modes, the heart experiences a totally opposite (to torsion) action—the right ventricle goes first and then left ventricle follows. Also, as we start from the apex of the right ventricle, circumferential and radial displacements do not occur at the beginning of the contraction, as it has to be, so the power of the contraction is seriously diminished. Despite its very simple explanation, it allows us to understand that the right heart pacing is absolutely contradictory to the heart physiology, and often results in development of the heart failure due to the right heart pacing. Evidence of this may be found in reported studies, one of which is the Geisinger study, "Permanent His Bundle Pacing Is Associated with Reduction in Morbidity and Mortality Compared to Right Ventricular Pacing: Results From Geisinger His Bundle Pacing Registry.", Mohamed Abdelrahman, MD, Dominik Beer, DO, Brendan Durr, DO, Angela Naperkowski, RN, CEPS, CCDS, Jess W. Oren, MD, Faiz A. Subzposh, MD, Gopi Dandamudi, MD and Pugazhendhi Vijayaraman, MD, FACC, 2018PRESENTATIONACC (AMERICAN COLLEGE OF CARDIOLOGY, www.crtonline.org/presentation-detail/permanent-his-bundle-pacing-is-associated-with-red. Cardiac resynchronisation systems or cardiac resynchronization therapy (CRT) have been developed, however, they are not an ideal decision because they provide stimulation of the two points within the heart chambers (which could be quite big—up to 500 ml in heart failure patients). (See Kenneth A. Ellenbogen, MD, y Pugazhendhi Vijayaraman, MD, "His Bundle Pacing. A New Promise in Heart Failure Therapy?", JACC: CLINICAL ELECTROPHYSIOLOGY, VOL. 1, NO. 6, 2015, December 2015:592-5).

A need exists for an improved method and system for treating heart conditions that can eliminate or reduce the drawbacks of the prior methods.

SUMMARY OF THE INVENTION

Methods, system and devices for treating and monitoring cardiac conditions, and, in particular, monitoring and treating bradyarrhythmias, tachyarrhythmias and heart failure, are provided. Some embodiments of the method, system and devices may also implement electrical energy harvesting from the heart, turning the kinematic energy of the heart into electrical energy. The electrical energy harvesting may be used to supply power to a pacemaker and/or pacing circuitry, or components thereof According to embodiments, the method may be carried out with the system and devices, which include two-chamber, three-chamber or other multi-chamber pacemakers for electrical stimulation of the heart with the function of frequency adaptation. Some embodiments may include as an optional feature, a microelectromechanical system (MEMS) for harvesting and converting the kinematic energy of the heart into electrical energy.

Another aspect of the method, system and devices provides a plurality of receivers arranged epicardially and containing an implantable element (e.g., electrode that may be inserted into the myocardium, such as via rotation or screwing motion), which relay signals and deliver electrical impulses to the heart. According to a preferred implementation, the receivers are controlled to deliver impulses in a sequence to replicate the heart's normal contraction function. A suitable control mechanism, actuated in or by the receiver and/or pacemaker or pacing circuitry, may regulate the delivery of impulses from the receivers. The contraction function of a normal functioning heart typically is a spiral movement from the apex toward the base. Pacing may be carried out at the respective receivers, consecutively, simultaneously, or combinations thereof (where some, e.g., one or more, pacing locations are simultaneously paced, and one or more other locations are consecutively paced). A receiver, for example, preferably may include a transceiver for receiving and transmitting signals, thereby allowing communications between the receiver and another component, such as the pacemaker or pacing circuitry. The receivers preferably deliver an electrical signal, delivered as an electrical impulse to the heart. The receivers also may receive and transmit signals to another circuit, which preferably is carried out wirelessly. The signals may be in addition to the electrical impulse signals delivered to the heart. For example, the other circuit may be a device that includes a control mechanism that controls the receivers. The receivers may communicate with a pacemaker that includes circuitry for generating and transmitting signals to the receivers, as well as receiving signals from the receivers. According to some alternate embodiments, one or more receivers may be configured to communicate with one or more other receivers, and may be synchronized to deliver electrical impulses to the heart at synchronized times, or at pre-determined time intervals, or another time-interval based on the sensed heart activity (sensed by the receivers), or in a consecutive pattern. According to some embodiments, receivers may be programmed to deliver an electrical impulse upon the receipt of an actuation signal (transmitted by another component, e.g., pacemaker or pacing circuitry, and received by the receiver).

According to preferred embodiments the receivers may be configured to wirelessly operate, and to generate their own power for operations from a power generation circuit or mechanism. According to some embodiments, the receivers are configured to convert acoustic or RF signals (waves), into electrical energy, which is stored or which may be immediately used for powering the receiver operations. A capacitor may be provided as part of the receiver for storing energy converted from the wireless signals, such as acoustic wave signals or RF signals.

The receiver operation may be controlled with the use of software that may generate screens for a user on a computing device, such as a computer, or tablet, to set sequencing and thresholds, and other parameters for the operation of the receivers, including when and under what conditions the impulse delivery should take place. According to some embodiments, the pacing circuitry of the pacemaker may be controlled to specify the parameters, and the pacing circuitry may operate the receivers accordingly.

According to some preferred embodiments, a device may be configured as a pacemaker comprising components for converting the kinetic energy of the heart movement into electrical energy. These devices utilize the electrical energy to stimulate the heart. According to a preferred embodiment, the device may be constructed with a housing and electronics situated within the housing. Some embodiments also may include the pacing circuitry to permit communications with receivers, as described herein in connection with the receiver operations in connection with other embodiments.

According to some embodiments, a pacemaker having a plurality of parts is provided. These embodiments provide that the body or case may be completely detached from the electrode and support to which the electrode is attached, or detached so as to permit rotation of the electrode (and its connected support) for implantation, separately from the case.

According to some of the multi-part pacemaker embodiments, the pacemaker preferably has at least one first part and at least one second part. The first part contains an electrode, which preferably is a spiral electrode constructed of memory metal that is implantable into the epicardium (and/or myocardium). The electrode is designed to be implanted by rotation of its spiral configuration. The pacemaker has a second part that comprises a case or housing that contains the pacemaker circuitry (e.g., electronics, software, modules, and the power supply). The electrode preferably is supported on a support or cover piece that rests on the endocardium when the electrode is implanted. Once the electrode is implanted, the pacemaker second part or case is implanted and/or connected to the first part to make an electrical connection between the electrode and the pacemaker circuitry within the second part or case. According to some of the preferred multi-part (e.g., two part) embodiments, the second part or case may hermetically seal therein the circuitry and components, and provide a connector or port for receiving an end of the electrode (of the first part). Alternate embodiments provide a connection to connect the first part and second part, which may comprise any suitable mechanism, such as detents, gaskets, or an outer flange. A septum or other receiving connector may be provided to receive the electrode end, and maintain the case contents in a sealed, and preferably a hermetically sealed, environment.

According to some preferred embodiments, the pacemaker has a housing or case that holds a reserve power source. The case also holds the electronics, which may include one or more components for operating the functions of the pacemaker and harvesting and converting energy from heart movements into electrical energy. For example, an electronics unit and/or circuitry and a MEMS may be included within the housing or case.

According to one exemplary embodiment, the pacemaker has a hermetically sealed titanium case of a cylindrical shape with a reserve power source, an electronics unit, and a MEMS for harvesting and converting the energy of the movement of the heart (kinetic energy) into electrical energy for stimulation of the heart.

Some embodiments may be configured as a pyramidal structure, which may comprise a pacemaker having a casing that is structured as a pyramid with rounded corners. According to some embodiments, the surface contacting the heart may be curved or arcuately shaped.

According to some preferred configurations, a pacemaker is provided with an electronics module having two circuits or circuit portions, one of which controls the pacemaker and the other of which controls the MEMS. Embodiments of the device may have 2 chips (micro-schemas), one of which controls the pacemaker, and the other controls MEMS. In this case, the operation of the microcircuits is also synchronized with each other. The micro-schemas may be embodied in one or more microcontrollers, which may include software containing instructions to process inputs received from electrodes and/or receivers in contact with the heart. According to some alternate embodiments, the pacemaker may have a third circuit or circuit portion. For example, if required for diagnosis or treatment of particular heart conditions, if necessary for the heart condition being addressed, it is possible to include a third chip (micro-schema) in the circuit to perform the functions that provide the detection of tachycardia, the recognition of the frequency of the pacing to treat the tachyarrhythmia, as well as switching to a backup power source and a mode of energy conservation (in this case, the transition to VVI-stimulation, where the ventricular chamber is being paced, and where the ventricular chamber also is being sensed, and where upon sensing a cardiac event, the device or portion thereof is inhibited). For the implementation of multi-chamber stimulation, the third chip (or circuit portion) regulates the function of synchronizing the work of different chambers of the heart—the atrium and ventricles, the right and left ventricles, "communication" between the receivers located in the thickness of the myocardium, regardless of their number. To do this, the control device (programmer) switches off and connects the required number of receivers. The third circuit portion may be embodied in a microcontroller, which may be the same microcontroller controlling the other functions of the pacemaker, or may be a separately provided microcontroller.

According to preferred embodiments, the pacemaker electronics or circuitry may include a portion configured to function in DDD modes, including DDDR modes, to deliver impulses to the atrial or ventricular chambers or both, as well as provide sensing of the atrium or ventricle or both. The pacemakers and devices shown and described herein, such as for example, the receivers, preferably are constructed to have resistance to MRI's.

Pacemakers according to some embodiments preferably may be configured with switching features which connects with the number of receivers positioned on the heart (e.g., with the receiver electrode positioned in the myocardium) suitable to provide the sensing data required to diagnose a condition or operating status of the heart.

The pacemakers and devices (e.g., receivers) preferably have a number of features, which may be provided as separate features, in combinations including one or more, or all features, together. The pacemakers and devices preferably may be configured to carry out a number of operative functions. For example, according to some embodiments, functions performed by the pacemaker and devices may include:

1. Stimulation of the selected heart chamber at a frequency of its own rhythm below a predetermined pace or beat.

2. Detection of tachyarrhythmias and selection of a frequency regime for "capture" and arresting of arrhythmia.

3. Detection of atrial premature beats and selection of a frequency regime for its suppression and prevention of tachyarrhythmia initiation.

4. Sequential stimulation of the heart chambers in the selected DDD/R mode.

5. Sequential or simultaneous stimulation of the ventricles of the heart in a given regime when performing resynchronizing therapy.

6. Detection of changes in the acid-base balance of the blood (tissue) surrounding the electrode for the realization of the function of frequency adaptation.

7. Sensors that may be used include those sensors that are suitable for detecting or measuring the parameter associated with the heart condition to be detected. For example, sensors may be provided to detect a physiologic change, such as, for example, body accelerations, paced QRS, impedance. Sensors also may be configured with programmable options. Examples of sensors that may be utilized in the pacemaker and receiver embodiments include suitable sensors, which may include the sensor types referenced in the publication Chu-Pak Lau, et al. "Evolution of pacing for Bradycardias: sensors", European Heart Journal Supplements (2007), 9 (Supplement 1)I11-I22, doi: 10.1093/eurheartj/sum057. Sensors may include those sensors used to sense activity, minute ventilation (MV), QT and others. In addition, sensors may include one or more rate adaptive sensors, such as, for example, those disclosed in the publication Chu-Pak Lau, "The Range of Sensors and Algorithms Used in Rate Adaptive Cardiac Pacing", PACE, vol. 15, August 1992, pp. 1177-1211. Sensors may include versions of sensors that currently exist for the implementation of DDDR.

8. Detection of changes in the movement (volume and frequency of movements) of the chest (lungs) for the executing of the rate responsive mode.

9. Determination and transmission of vector data (displacement direction) and degree (the distance to which is shifted) of the receiver installed in the given chamber for:

a. Assessment of the possibility of collecting energy—it is meant how dynamically the site moves to serve as a source for collecting energy (need to be proved in clinics). Now this work performed in experiments and by noninvasive Echo post processing program (VVI—velocity vector imaging)

b. Determining when this area of the heart should be stimulated to optimize the pump function of the heart According to some alternate embodiments, receivers not only sense and deliver electrical impulses to the heart, but also may be configured with a built-in injector that delivers a treatment agent to the heart. For example, the receiver injector may locally spread a drug (e.g., such as Amiodarone) to treat arrhythmias, or deliver another treatment drug.

According to some alternate embodiments, the surface of the receiver and/or electrode is covered with a thin layer of a chemical (e.g., such as a treatment agent), for slow or controlled release. For example, the receiver or electrode may slowly release a dexamethasone hormone.

Some embodiments may include a mode switch that provides a rate control feature designed to prevent the tracking of paroxysmal atrial tachycardias. The feature may be performed by placing the device in DDIR mode until the episode is over, preventing a rapid ventricular paced rate in response to the rapid atrial rate.

These functions may be provided separately or in combination with each other, with a pacemaker being configured to have one or more of these functions.

BRIEF DESCRIPTION OF THE DRAWING FIGURES

DETAILED DESCRIPTION OF THE INVENTION

A method, system and device is provided for treating and monitoring cardiac conditions, which involve providing a plurality of receivers arrangeable on the heart, and being wirelessly actuated and powered to deliver electrical impulses at locations of the heart at predetermined or desired time intervals, which may be in response to a sensed condition of the heart. The method, system and devices are utilized to treat and monitor conditions of the heart, among which may include bradyarrhythmias, tachyarrhythmias and heart failure. Some embodiments of the devices and systems provide a pacemaker device configured to harvest energy as it implements the pacemaker functions.

The devices are configured with circuitry and/or components that generate electrical impulses, and monitor electrical signals from sensor positions at the heart. For example, the system and devices may include chips containing software with instructions for obtaining information from the heart, monitoring and processing information, and generating electrical pulses that may be relayed to the heart at one or more locations where electrodes of the receiver devices are situated.

Some embodiments of the method, system and devices also may include an element and coupled circuitry for converting kinetic energy from the heart movements into electrical energy. The method, system and devices carry out electrical energy harvesting from the heart, turning the kinematic energy of the heart into electrical energy.

Figure 2A:
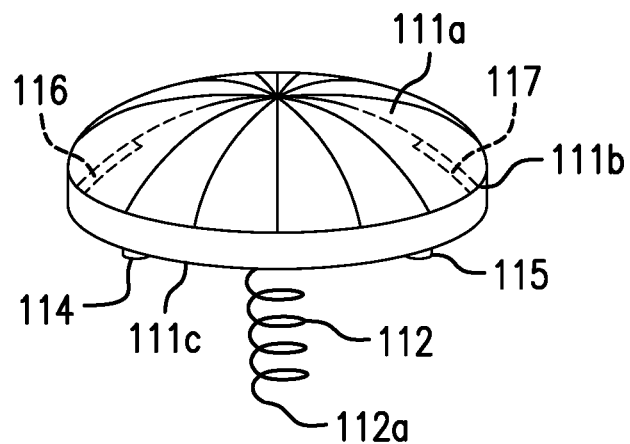
FIG. 2A is a perspective view of an exemplary embodiment of a pacemaker according to the invention.

Referring to FIG. 2A, according to an exemplary embodiment, a pacemaker 110 is shown provided having a case 111. The case 111 according to some preferred embodiments, has at least one electrode 112 for delivering electrical impulses to the heart, and in particular the epicardium.

In the center of the pacemaker's body (case 111), there is a spiral-shaped electrode 112 for feeding stimulation pulses to the epicardium. The spiral shape provides the so-called. "active" fixation of the electrode 112. Another electrode is the electrically conductive body 111 of the pacemaker 110. (Preferably, other pacemaker embodiments depicted and described herein also provide for the pacemaker body or casing to function as an electrode.) Implantation of the pacemaker 110 requires clean operating room. At the working heart, epicardial implantation of the device 110 may be carried out from thoracoscopic, mini-thoracotomy access (or median sternotomy after the completion of the main stage of the operation for the underlying pathology), which may be performed under general anesthesia (as well as other variants of anesthesia, —such as implantation from subxyfoidal access which allows performing the procedure under local anesthesia. An example of a suitable implantation technique, via a subxiphoid approach is disclosed in the publication Sertac Haydin, M. D., et al. "Sub xiphoid Approach to Epicardial Implantation of Implantable Cardioverter Defibrillators in Children", PACE, Vol. 00, (2013) pp. 1-5; and Roberto Costa, et al. "Minimally Invasive Epicardial Pacemaker Implantation in Neonates with Congenital Heart Block", Arq. Bras Cardiol. (2017), 109(4), pp. 331-339. At the moment of implantation, according to a preferred implementation, the device 110 is screwed in (e.g., about 8-10 turns clockwise) in the vessel-free area of the epicardium, then it is preferred to have additional fixation of the device 110 which is done by sewing with ligatures (strands), such as, for example, synthetic, monofilament, nonabsorbable polypropylene suture (e.g., one type being commercially available under the brand PROLENE®) for which there are 4 staples (e.g., 114, 115, 116, 117) on the body of the pacemaker 110. Other numbers of staples or connecting points may be provided on the pacemaker 110 for attachment to the heart.

According to preferred embodiments, the electrode 112 is made of metal having a memory. The last turn leads to the exit of the tip 112a of the electrode to the surface of the ENDOCARD (i.e., the endocardium, which is the innermost layer of tissue that lines the chambers of the heart), and, according to preferred embodiments, where the electrode is provided with hooks, in the next move the hooks are released for additional fixation and mostly to improve the pacing thresholds and sensitivity.

Frequency Adaptation Sensors:

The device preferably includes sensors, among which comprise frequency adaptation sensors. The sensors detect electrical signals which may be processed and analyzed to determine the parameters of the patient's body movement, including the step frequency, speed, lift, descent, etc., and the position of the body in space, for example, horizontal— during sleep. These sensors may include, but are not limited to GPS, gyroscope, rotation sensors and accelerometer sensors. Examples of sensors are disclosed in the publications attached as Appendices A and B hereto.

Power Source and Charging:

The device is configured with a power source. Presently, the model presented, such as the device 110, uses a battery, such as for example, a lithium fluorine carbon battery, which is inserted into the case 111. According to embodiments where the pacemaker 110 is powered by the conversion of kinetic motion of the heart and the MEMS, the battery may serve as a backup power source. According to preferred embodiments where power is obtained from the conversion of kinetic motions of the heart, the battery size is reduced. Reducing the size of the battery preferably reduces its size and "makes room" for MEMS.

As a source for recharging the battery of the EKS in the present devices, according to a preferred implementation, the principle of electromagnetic induction is used, which is realized due to the introduction of an inertial converter into the design. In this case, the receiving induction and transmission coils are located in the body 111 of the pacemaker 110.

Figure 3:
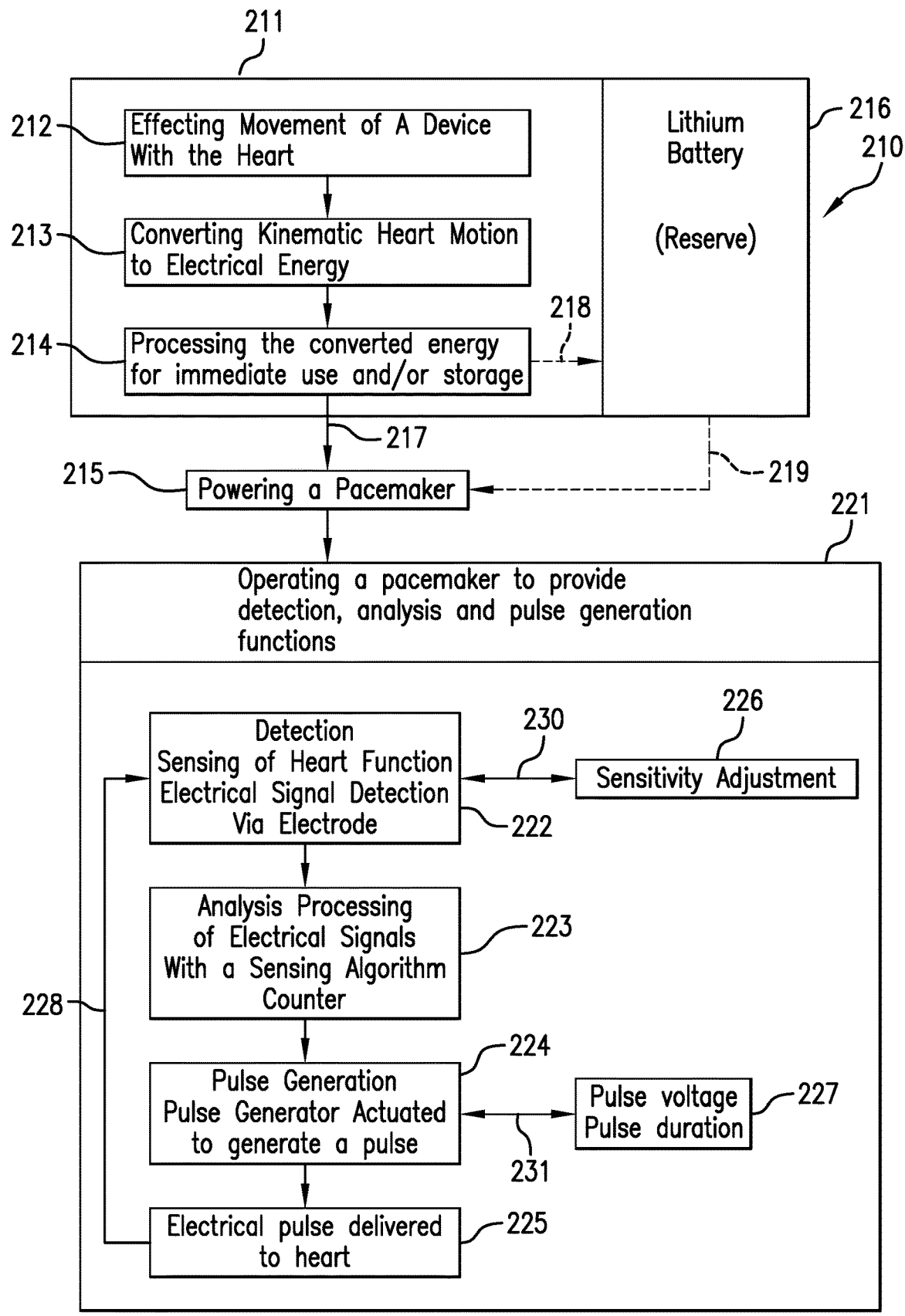
FIG. 3 is a flow diagram depicting an exemplary implementation of a pacing method with the energy conversion feature.

Referring to FIG. 3, an exemplary embodiment depicting a system and method 210 for carrying out kinematic energy harvesting and conversion is illustrated in a schematic diagram. The system and method 210 preferably are carried out with a device that is situated to receive physical movements from the heart. According to preferred implementations the device is configured with pacemaking features and is situated on the heart. The device and its operations are powered by a power source, block 211, which powers a pacemaker, block 215. Movement of the device is effected through the kinematic motion of the heart (e.g., heart beats), block 212. A circuit is provided, and preferably includes a microelectronic mechanical unit or component, such as a MEMS, that converts the heart motion into electrical energy, block 213. The electrical energy is processed, block 214, so it may be used immediately to power the pacemaker and the pacemaking functions portion of the pacemaker device (see block 221), as represented by path 217 and, alternatively, or additionally may be processed to provide electrical energy to a battery 216 for storage (e.g., to charge the battery 216), as represented by path 218. The battery 216 may provide the electrical power to the pacemaker, represented by path 219, and/or may be used as a reserve or back up source, when the kinematic functions are unable to provide or meet the power demand.

Referring to FIG. 3, the pacemaker is powered, block 215, utilizing the power generated by the harvesting and converting operations (in block 211). Additionally or alternately, there is a battery 216. Exemplary operations associated with the pacemaker are depicted in block 221, where detection, block 222, analysis, block 223, and pulse generation, block 224, are carried out to produce an electrical pulse that is delivered to the heart, block 225. The detection, block 222, senses the heart function and detects the activity by sensing the electrical activity of the heart, typically with an electrode placed on or within the heart. The detection, block 222, may be regulated by adjusting the sensitivity, represented by block 226 sensitivity adjustment, and represented by the path 230, so a high or low threshold is required, or some other adjustment. The pulse generation, block 224, may be regulated by adjusting the voltage and pulse duration, block 227, and represented by the path 231. When signals are detected from the heart functions, the signals are analyzed, block 223. The analysis of the signals typically involves processing the signals with a sensing algorithm, and a counter, block 223. The analysis may result in the processing of the signals which depict normally operating heart activity. However, in some instances, the heart activity may become outside of the normal expected function, and the processing of the signals reveals this. The analysis therefore actuates a pulse generator to generate a pulse, block 224. The pulse that is generated is sent to the heart (the location where an electrode may be positioned), block 225. The pacemaker continues the cycle of operations, as represented by path 228, detecting, block 222, analyzing, block 223, and generating pulses, block 224, and delivering electrical pulses to the heart, block 225, as required. According to the embodiments, the pacemaking operations are carried out with the device, which includes pacemaker circuitry, and power components that convert the heart kinematic motion into electrical energy to support the pacemaker operations.

Figure 2B:
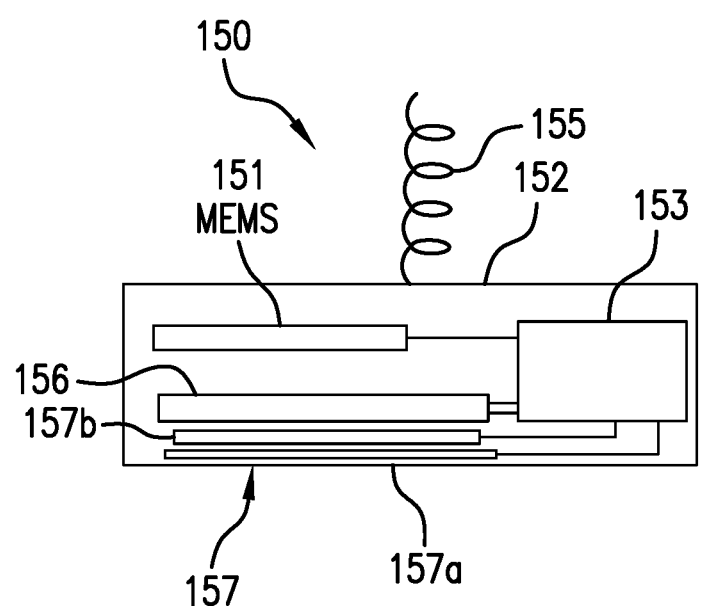
FIG. 2B is an alternate embodiment of a pacemaker shown schematically to depict an exemplary embodiment of circuitry.

According to a preferred alternate embodiment, as depicted in FIG. 2B, a device 150 is shown configured with a first circuit arrangement that includes a microelectronic mechanical unit or component, such as a MEMS 151, that converts the heart motion experienced by the MEMS 151 into electrical energy. The device 150 is represented schematically, and, according to one implementation, may be embodied in the form of pacemaker, including for example, the pacemaker device 110 depicted in FIG. 2A. The device 150 preferably is configured as a pacemaker with pacemaking functions that are programmed to the circuitry and memory of the device 150, or that may be programmed into the device 150 or adjusted for the type of pacing operation desired. The programming may be carried out through a wireless or wired linkage, and may be programmed or adjusted prior to, during or after implantation. The device 150 also is configured with detection features to detect heart functions and conditions that may be sensed electrically. In the embodiment of the device 150 shown, a case 152 (similar to the case 111 in FIG. 2A) is represented and surrounds and may support the components therein. The case 152 is configured to engage the heart, so that the device 150 experiences movement as the heart moves, (e.g., beats or pulses). The transfer of energy from the heart to the MEMS 151 is processed and converted into electrical energy. This is accomplished with the circuitry of the MEMS 151.

The circuit preferably includes one or more processing components (such as, for example, a microprocessor, a microcontroller) configured with instructions to convert the energy to a suitable form (voltage) that may be used to power the pacemaker circuitry. The pacemaker circuitry is represented by the pacing circuit 153, which preferably includes detecting circuitry for detecting heart operation and functions, and circuitry for processing and analysis of the detected signals. The device 150 preferably includes at least one contact point, serving as an electrode, such as for example, the electrode 112 shown in FIG. 2A. According to some embodiments, the device 150 preferably is wireless in regard to the delivery of electrical impulses. (Alternatively, one or more leads that contact the heart may be provided.) According to a preferred embodiment, the electrode is configured to engage the heart and is insertable through the heart. In the embodiment depicted in FIG. 2A, the electrode 112 is spiral shaped, and has an end with a leading tip 112a. The device 150, when configured with an electrode, such as the spiral electrode 112 of FIG. 2A, may be implanted into the heart by rotation of the device 150. Similar to the embodiment shown and described in connection with FIG. 2A, the electrode 155 is sealed to the device 150, so that the case 152 seals the electronic components and/or circuitry 153, as well as the power generation elements, and/or battery 156, and the entry location of the electrode 155.

According to some embodiments, the pacemaker may be configured having a wire lead extending from the main body or case. According to preferred embodiments, the pacemaker may be configured as a wireless or leadless pacemaker.

Referring to FIG. 2A, the case 111 is shown having a top 111a and a sidewall 111b, with the electrode 112 disposed on the side 111c opposite the curved or rounded surface 111a.

Referring to FIG. 2B, a pacemaker 150 is shown schematically to depict an exemplary embodiment of circuitry 153, which may include one or more chips, microprocessors, microcontrollers, a MEMS 151, as well as a battery 156, and induction circuitry 157 for charging the battery, the induction circuitry being shown comprising a primary induction coil 157a and a secondary induction coil 157b arranged for electromagnetic charging of the battery 156.

Figure 2C:
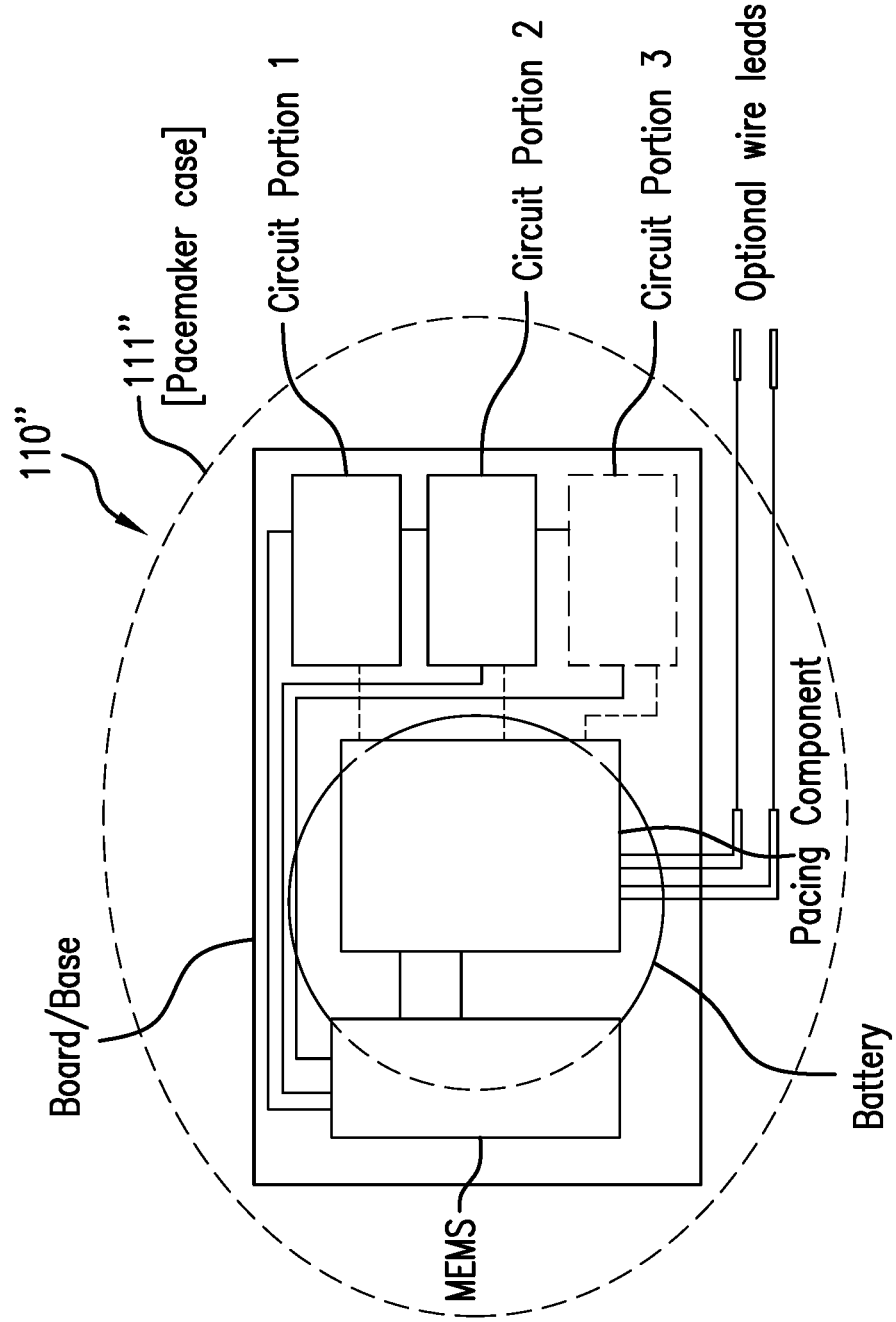
FIG. 2C is an alternate embodiment of a pacemaker depicting an alternate configuration representing pacing circuitry.

Referring to FIG. 2C, an alternate configuration for the pacing circuitry is depicted, with a plurality of circuitry portions represented, including a first circuit portion, a second circuit portion, and a third circuit portion. A MEMS unit also is depicted, along with a battery, and optional leads (which are not provided where a wireless communications are transmitted between the pacemaker and receivers). Preferably, induction charging may be used to charge the battery, and an induction circuit may be provided within the pacemaker circuitry (such as, for example, the coils 157a, 157b shown and described herein).

In FIG. 2C, another exemplary embodiment of a pacemaker 110" is depicted in a schematic view. The pacemaker 110" has a case 111" and is provided with an electronics module having two circuits or circuit portions, a first circuit portion (Circuit portion 1) and a second circuit portion (Circuit portion 2). The case 111" is represented schematically in outline form as an oval, but may comprise another suitable shape, such as, for example, a circle, or any shapes shown or described herein, or other geometry. The pacemaker 110" also includes a MEMS. In the embodiment depicted, one of the circuit portions controls the pacemaker operations and the other circuit portion controls the MEMS. The circuit portions may be embodied in one or more chips (micro schemas), microprocessors, microcontrollers. In the schematic illustration represented in FIG. 2C, there are 2 chips (micro-schemas), representing Circuit portion 1, and Circuit portion 2. Circuit portion 1 controls the pacemaker pacing operations, and Circuit portion 2 controls the MEMS. The circuitry also preferably includes a timer or clock that is integrated in the circuitry or may be separately provided and coupled to the chips, controllers or circuit portions. The operation of the microcircuits, such as, for example, Circuit portion 1 and Circuit portion 2, preferably are coupled together directly or through another processing component (e.g., microprocessor or microcontroller) and are synchronized with each other. Software containing instructions to carry out processing of pacing data and pacing operations (e.g., delivery of electrical impulses), preferably is provided on the chips or circuit portions (e.g., on a microcontroller or microprocessor). For example, the micro-schemas may be embodied in one or more microcontrollers, which may include software containing instructions to process inputs received from electrodes and/or wireless receivers in contact with the heart.

Further referring to FIG. 2C, according to some alternate embodiments, the pacemaker 110" may have a third circuit or circuit portion (represented by Circuit portion 3). The third circuit portion preferably is coupled together with the other circuit portions, and may be used to detect heart conditions, such as, for example, detecting a tachycardia. The third circuit portion may be configured with software that includes instructions for processing information to detect the recognition of the frequency of the pacing and generate a response to treat the tachyarrhythmia (e.g., via another of the pacing components or functions of the pacing circuitry). The third circuit portion may be configured to regulate switching to a backup power source and a mode of energy conservation (in this case, the transition to VVI-stimulation, where the ventricular chamber is being paced, and where the ventricular chamber also is being sensed, and whereupon sensing a cardiac event, the device or portion thereof is inhibited). According to some embodiments, the third circuit portion may be configured with software containing instructions to implement multi-chamber stimulation, and regulate the function of synchronizing the work of different chambers of the heart—the atrium and ventricles, the right and left ventricles, via "communication" between the receivers located in the thickness of the myocardium, regardless of their number.

To do this, the control device (programmer) switches off and connects the required number of receivers (which may be wireless stimulation devices placed in desired locations of the heart). The third circuit portion may be embodied in a microcontroller, which may be the same microcontroller controlling the other functions of the pacemaker, or may be a separately provided microcontroller. Similarly, although referred to as circuit portions, the circuit portions may be embodied in one or more separate chips (or microcontrollers or microprocessors), or may be configured in a single unit.

Although referred to as a receiver, or receivers, preferably each receiver also includes a sensor and/or has sensing functionality, so that the receivers, in addition to the delivery of electrical pulses or stimuli to the heart, also sense heart activity, and relay signals corresponding to the heart activity to the processing circuitry, such as, for example, the pacemaker and circuitry therein (e.g., pacing circuitry). Preferably, the sensor or sensing function is provided as part of the receiver, and, preferably, is paired therewith.

Although the pacemaker 110, 110" (FIGS. 2A and 10) is depicted in a preferably pyramidal configuration, alternatively, the body of the pacemaker may be shaped in other configurations having rounded or smoothed corners.

In conjunction with methods, systems and devices, some embodiments and implementations may include a pacemaker that has one or more removably detachable components. According to a preferred embodiment, a pacemaker is provided having multiple parts, including a first part that allows implantation into the heart tissue (e.g., epicardium and myocardium and/or endocardium), and a second part that connects with the first part when the first part is implanted. Exemplary embodiments depicted herein illustrate a first part comprising an electrode and support or cover, and a second part comprising a base. The first part is installed in position on the heart, preferably by rotation, and after it is in its desired location, the second part is connected to the first part. The implantation procedure may be carried out using any suitable technique, including median sternotomy, or lesser invasive procedures such as thoracoscopy. The first part, as well as the second part, may have an installation feature for facilitating installation using an instrument. For example, one or more recesses or bores may be provided in the first part, or second part, or in each, to fit a mating end of an installation tool, which may be used to install, and/or rotate the pacemaker parts into position. Some exemplary embodiments are discussed herein.

Implantation of the pacemaker may comprise implanting the first part, by rotating the electrode into the heart, so that the first part rests on the heart surface (e.g., endocardium). The first part electrode preferably serves as a cathode, while the first part cover portion serves as an anode, and when the cover portion is resting on the heart surface, it provides electrical conductivity with the heart surface. The cover portion or anode portion is electrically insulated from the electrode carried thereby. Implantation of the first part may be followed by maneuvering the second part, such as the case, to the same location to connect it with the first part. Although median sternotomy procedures may be employed, preferably, the pacemaker implantation procedure may be carried out thoracoscopically, using a thoracoscope to implant the pacemaker first and second parts.

Pacemakers discussed and disclosed herein may also be configured with an energy harvesting feature that is designed to convert the heart kinematic motion into electrical energy. The pacemaker device may be configured to harvest energy as it implements the pacemaker functions. The electrical energy may be used to power one or more functions or operations of the pacemaker, or associated circuitry. The pacemakers and other components shown and described herein may be utilized for treating and monitoring cardiac conditions. The method, system and devices are utilized to treat and monitor conditions of the heart, among which may include bradyarrhythmias, tachyarrhythmias and heart failure.

The pacemaker preferably is configured with circuitry and/or components that generate electrical impulses or direct the actuation of electrical impulses at other locations (e.g., locations remote from the pacemaker location, such as a location of the heart where one or more associated components are positioned, e.g., receivers). Pacemaker embodiments may be configured with circuitry and software which enable the pacemaker to monitor electrical signals from sensors positioned at the heart. For example, chips containing software with instructions for obtaining information from the heart, monitoring and processing information, and generating electrical pulses that may be relayed to the heart at one or more locations where electrodes of the device are situated (i.e., receiver locations).

Figure 2D:
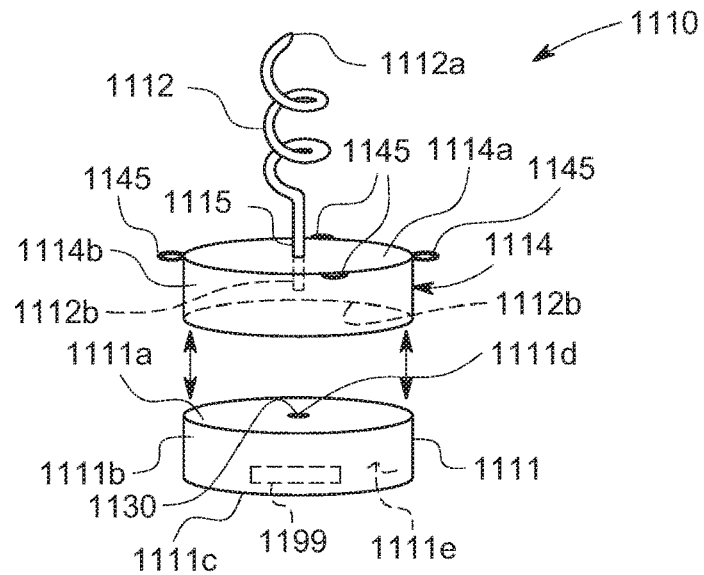
FIG. 2D is a perspective view of an exemplary embodiment of a pacemaker according to the invention, where the electrode and cover are detachably provided relative to a base.

According to an exemplary embodiment, an alternate embodiment of a pacemaker 1110 is illustrated. The pacemaker 1110 may be configured with circuitry and carry out operations as shown and described in connection with other pacemakers discussed herein, such as, for example, the pacemakers 110 and 310, including operations in connection with receivers (see e.g., FIGS. 4-8). The pacemaker 1110 is configured with one or more detachable components that facilitates installation of the pacemaker 1110 at the heart site location, i.e., which may be the implantation site. The detachable components, preferably may comprise a top or cover and a bottom or case. The pacemaker 1110, in a preferred embodiment illustrated in FIG. 2D, is provided having a bottom or case 1111 and a cover 1114. The cover 1114, according to preferred embodiments, has at least one electrode 1112 for delivering electrical impulses to the heart, and in particular the epicardium. According to some embodiments, the pacemaker 1110 may be provided as a unit, and may be configured for installation as a unit (which may be a first optional configuration). The pacemaker 1110 also includes a second optional configuration that allows for implantation or installation to take place by installing one or more of the pacemaker components (e.g., one or more of the detachable components), separate from the other components or component. Although preferred embodiments have been illustrated, the pacemaker parts, such as the first part and second part, may be connectable through a suitable connecting mechanism, which may comprise threads on each part, a threaded post and socket, friction fit, quick connect/disconnect mechanisms, and other suitable connectors.

In the embodiment illustrated in FIG. 2D, according to a preferred configuration, the pacemaker 1110 is shown having a detachably provided electrode 1112. The detachably provided electrode 1112 may be connected with a base or other support, such as the top or cover 1114, to facilitate installation or implantation of the electrode at the heart location, as well as to facilitate connection of the electrode with the pacemaker body or second part (e.g., case 1111), and preferably the circuitry 1199 within the case 1111. Installation of the pacemaker 1110 preferably involves implanting the electrode 1112 in the heart, e.g., such as through the epicardium. According to some embodiments, the pacemaker electrode 1112 may be removably attachable to and detachable from the pacemaker case 1111 (and the circuitry of the pacemaker, e.g., which preferably is within the case, to which the electrode electrically connects). The case 1111 preferably houses electronics and/or circuitry, which may include pulse generating circuitry, software, memory, power supply (battery), and/or other typical pacemaker circuit components, as well as signal processing and generating electronics, to communicate with the receivers (i.e., sensors) when the pacemaker 1110 is used with the receivers shown and described herein). The case 1111, when connected with the electrode 1112 (or supporting structure to which the electrode may be mounted or carried, such as the support or case cover 1114), makes an electrical connection between the electrode 1112 and the circuitry (and/or electronics within the case 1111). The pacemaker 1110 may therefore be assembled together, e.g., by connecting the case 1111 with the cover or support 1114 to form an electrical connection between the electrode 1112 and the case circuitry 1199.

According to some preferred procedures, the assembly of the second component with the first component may be carried out in vivo, allowing replacements of a battery or other component, while permitting the first part, the electrode 1112 and cover 1114 to remain installed on the heart. The case 1112, or a new case 1112, may be reinstalled or installed by connecting it with the already present cover 1114 and electrode (e.g., which were allowed to remain when the second part, case 1111, was removed).

According to a preferred implementation, the electrode 1112, and base or support 1111 to which it may be attached, may be implanted into the heart using a suitable implantation method or technique. Although the pacemaker 1110 may be implanted through a median sternotomy procedure, preferably, the pacemaker 1110 may be implanted using lesser invasive thoracoscopic, or mini-thoracotomy access techniques. According to preferred implementations, the pacemaker electrode 1112, and base or supporting structure to which it is connected, e.g., support 1114, may be guided and/or maneuvered to the location of the heart for installation using a thoracoscope. When at the desired location, the electrode 1112 may be implanted by rotation of the electrode 1112 to pierce the heart tissue (endocardium), and further rotating the electrode 1112 to insert the electrode 1112 into the heart tissue (myocardium and/or epicardium). According to preferred implantation procedures, the electrode portion of the pacemaker is implanted into the epicardium (which lines the heart chambers). Once the electrode 1112 has been inserted to the desired depth of penetration, the support 1114 preferably rests on the heart surface or endocardium. The electrode 1112 may be provided having a desired length for a desired penetration depth at the implant site. Preferably, in addition to the implantable electrode 1112, another electrode is present, and in the embodiments, preferably, the case body 1111 serves as a further electrode or second electrode, and preferably an anode, with the first electrode 1112 serving as a cathode. The pacemaker body 1111 according to some preferred embodiments may contact or connect with the pacing circuitry housed within the case 1111. The body 1111 also preferably connects with the top or cover 1114 so that there is electrical conductivity between the heart (i.e., the heart surface on which the cover 1114 rests) and the pacemaker circuitry. The electrode 1112 preferably remains electrically insulated from the cover surface (or anode) 1114, and case body 1111.

According to a preferred embodiment illustrated in FIG. 2D, the pacemaker is shown with the electrode 1112 provided in the center of the pacemaker body (case 1111). The electrode 1112 is shown situated on the support or case cover 1114. The case cover 1114 preferably includes or is fitted with an insulated seal 1115, through which an end of the spiral-shaped electrode 1112 passes to make an electrical connection with the circuitry housed within the pacemaker 1110, and in particular, the pacemaker case 1111. The circuitry, represented schematically as reference or block 1199, is configured to feed stimulation pulses to the heart, and preferably the epicardium, via the electrode 1112. The spiral shape of the electrode 1112 provides the so-called "active" fixation of the electrode 1112 (although as discussed additionally, according to alternate embodiments, additional mounting elements, such as hooks and/or ligatures may be used to further provide fixation of the pacemaker and electrode).

Once the electrode portion of the pacemaker 1110 has been installed, e.g., by screwing the spiral electrode 1112 into the heart (e.g., epicardium and/or myocardium), the additional component or components, such as, in the preferred embodiment, the pacemaker detachable case 1111 (and the electronics and circuitry therein) is installed. Preferably, this is done by implanting the second pacemaker part, (e.g., the case 1111) at the heart site. According to a preferred implementation, the case 1111 is supplied to the location of the electrode 1112 and case cover 1114 (which are already held in a location on the heart through the rotation of the spiral electrode), using a suitable implantation procedure, e.g., sternotomy, thoracoscopy, or the like. The case 1111 is then connected to the support or case cover 1114. The case 1111 preferably is aligned with the support or case cover 1114, and, may for example, be viewed with a camera and/or light of a scope, such as a fiber optic camera or light, which may be part of the thoracoscope or a separate accessory. The first part and second part of the pacemaker 1110 are connected together to effect electrical contact between the electrode 1112 and the pacemaker circuitry 1199 within the case 1111 (the first part, for example, being the electrode 1112 and associated case cover 1114 or support) and the second part, for example, being the case 1111. The electrode 1112 preferably makes the electrical connection with the pacemaker circuitry 1199 housed in the case 1111, so that pulses may be delivered through the electrode 1112 to the heart.

The case 1111 may be installed using a procedure similar to the procedure used to install and implant the electrode 1112 and cover part 1114, which for example, may be a median sternotomy procedure, thoracoscopic, or mini-thoracotomy access, or combinations of these procedures, or other suitable procedures. According to a preferred embodiment, the thoracoscope may be used to implant the first part of the pacemaker 1110, which may comprise the electrode 1112 and support such as the case cover 1114, and then follow the electrode implantation with the implantation of the second part (or additional parts), by preferably using the thoracoscope to install the pacemaker case 1111 and connect the case 1111 to the case cover 1114.

According to preferred embodiments, a suitable connecting mechanism may be provided, such as threads, ratchet, hooks, friction fit, or other connecting elements, that facilitate the connection between the support or case cover 1114 and the case 1111. The case cover 1114 and case 1111 preferably may include a sealing gasket 1130 that provides a suitable barrier to entry (e.g., of fluids and other material in the implantation environment) into the case space 1111e where the electronics and circuitry components reside. Alternatively, or in addition, the electronics and circuitry may be sealed so that any intrusion of fluids into the case 1111 will not affect the operation of the device 1110. The electronics and/or circuitry seal may be a separate seal, and may be in addition to the sealing gasket sealing the case space 1111e.

According to some preferred embodiments, the case 1111 preferably includes a top wall 1111a, which is formed with or sealed together with one or more side and/or bottom walls. In the exemplary embodiment depicted, the case 1111 is shown with a sidewall 1111b, and a bottom wall 1111c. The pacemaker 1110 may be constructed with the second part or case 1111 provided with a top wall 1111a which with the other walls or boundaries of the case 1111 (e.g., side wall 1111b and bottom wall 1111c), seals the case components and circuitry therein. Preferably, the seal is a hermetic seal. A receiving area, such as the opening 1111d in the top wall 1111a, is provided to receive the electrode end 1112b. Preferably, the opening 1111d has an electrical socket or other connector that is electrically connected with the circuitry 1199 in the case 1111, and which also connects with the electrode end 1112b to make an electrical connection between the electrode 1112 and the pacemaker circuitry (in the case 1111). The case 1111 preferably carries the circuitry and electronics (such as a pulse generator, and/or circuitry described herein and depicted in the figures), where they are hermetically sealed against the outside environment. A suitable sealing method or structure may be employed to hermetically seal the case walls or boundaries (e.g., 1111a, 1111b, 1111c and opening 1111d), such as laser welding, epoxy or other bonding material, or combinations of these. Other suitable materials and methods may be used to produce the case 1111. For example, the case 1111 may be produced with the use of a laser whose beam is used to produce a hermetic seal that is airtight and liquid-tight. Laser welding may be used to secure one or more walls of the case. In addition, as a further sealing provision, after welding of one or more walls together, such as, for example, the top wall 1111a, or bottom wall 1111c to the side wall 1111b), the pacemaker body 1111 may be covered in a thin layer of plastic (e.g., epoxy plastic). The top surface of the top wall 1111a however, may entirely, or partially remain free of a coating (e.g., epoxy), or include a masked out portion to prevent blockage of any surface, port or structure to which the electrode 1112 attaches, or passes through.

The electrode 1112 makes a connection with the circuitry within the case 1111 through a suitable connection. According to preferred embodiments, the connection may comprise a connector through which the electrical connection between the electrode 1112 and case circuitry is made. For example, according to some embodiments, the connector may comprise a terminal or port (e.g., 1111d) in the top wall 1111a of the case 1111. According to an exemplary embodiment, the case top wall 1111a preferably includes a connector 1130 or opening through which the connecting end 1112b of the electrode 1112 may pass. A seal or gasket may surround the connector 1130 to seal the case interior from the outside (hermetic seal), and receive the electrode 1112 when the second part, e.g., the case 1111 is installed and connected to the already implanted first part (e.g., the electrode 1112 and case cover 1114). The connector 1130 may be sealed with an epoxy or laser weld, or other suitable seal or procedure to make a seal with the case 1111, for example, in particular the case top wall 1111a. According to some optional configurations, a silicone or other gasket may seal the area where the connector portion that is designed to connect with the electrode end 1112b, thus providing a seal of the case and a second seal of the connector or connector portion that will receive the electrode end 1112b. According to some preferred embodiments, at least a portion of the case connector that connects with the electrode 1112, such as for example the connector 1130, has at least a portion that electrically communicates with the case circuitry, which may be present within or makes a connection with the sealed environment (e.g., of the case), and at least another portion that is outside of the sealed case environment (that connects with the electrode end). The connection may be within the environment sealed between the case exterior and cover interior.

Alternatively, according to some alternate embodiments, the electrode end 1112*b* may include a connector at its connecting end 1112*b*, and the case cover 1111*a* may include a connector such as the connector 1130, which may be configured as a mating connector that connects with the electrode end 1112*b* or a connector provided on the electrode end 1112*b*. This connection provides electrical conductivity between the heart via the electrode 1112 and the circuitry within the case 1111 that the connector 1130 connects with. Some exemplary embodiments are depicted herein and may be utilized in the arrangement depicted in FIG. 2D.

The second part or case 1111 connects to the first part using a suitable connection means. One example of a connection is a friction fit, where the first part or second part includes an outer wall that is received within the wall of the other. The second part may be lowered or inserted into the first part to form the connection. Alternatively, or in addition, the parts may be magnetically attached, which may be done by providing one or more magnets or magnetic surfaces on each of the first part and second part that may connect when they are in proximity (e.g., when the second part is moved close to the first part). The magnets may be embedded into the cover (e.g., 1114) and preferably the underside surface thereof, and provided on the outer surface of the case (e.g., 1114). Alternatively, the cover or flange walls of a cover (or a portion or portions thereof) and top wall or side wall of the cases (or a portion or portions thereof), may be magnetic, and provided having polarity to mate with and secure the case and cover together. In these embodiments (e.g., using friction fit or magnetic attachment), removal of the second part may be effected by pulling the case 1111 in a direction away from the cover 1114 and/or by rotating it to overcome the attractive magnetic and/or frictional forces holding the parts together, and may be done using a suitable tool. The case wall (e.g., 1111*b*) may be provided with a structure, e.g., a recess, or detent, or flange, to facilitate effecting withdrawal of the case 1111 from the cover 1114 using a suitable tool that is able to grasp the case and separate it from the cover 1114. The tool may be a thoracoscopic tool that may be operated from outside of the body or cavity where the pacemaker 1110 is installed. For example, the tool may include fingers that grasp to a recess or detent of the case 1111 so that retraction of the tool will remove the case 1111 from the cover 1114 (allowing the cover 1114 and its electrode 1112 to remain implanted, while the case 1111 is removed). According to some other embodiments or implementations, rotation of the case with a tool may be used to detach the case from the cover. See e.g., FIGS. 2H and 2I.

The pacemaker 1110, including the case 1111, and support or case cover 1114 may be constructed from any suitable material. One suitable material is titanium or a titanium alloy. Other materials, may include any suitable pharmacologically inert, non-toxic, sterilizable material that is biocompatible, and is able to function in the environmental conditions of the body. The electrode 1112, preferably like the electrode 112, is constructed from a metal having a memory.

In the embodiment depicted, in addition to the detachable electrode 1112, another electrode is the electrically conductive body or case 1111 of the pacemaker 1110. As discussed herein in connection with the pacemaker 110, the pacemaker 1110 may include one or more mounting points, for suitable ligatures to hold the pacemaker to the heart. Preferably the mounting points may comprise eyes 1145 (FIG. 2D) affixed to the pacemaker part or portion closest to the heart, such as for example the top portion 1114 of the pacemaker 1110. The device portion that includes the electrode 1112 and case cover 1114 is screwed in (e.g., 8-10 turns clockwise, for example) in the vessel-free area of the epicardium, and then additional fixation of the device 1110 may be done by sewing with sutures or ligatures (strands), such as prolene ligatures, using the attachment points or eyes 1145 on the pacemaker 1112. According to a preferred embodiment a plurality of attachment points 1145 are provided on the pacemaker case 1111. Some embodiments may employ staples and/or other connectors (e.g., such as, for example, 4 staples or mounting points) on the body or case 1111 of the pacemaker 1110.

Figure 2E:
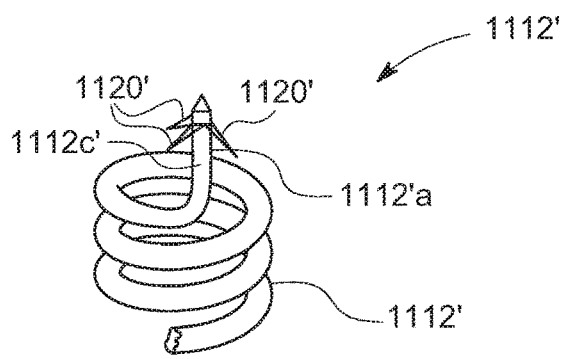
FIG. 2E is a perspective view of an electrode shown, shown in partial view, having an alternate electrode tip end with optional hooks.

According to some alternate embodiments, the pacemakers shown and described herein may be provided with an additional secondary mounting feature. Referring to FIG. 2E, the electrode which, as shown in the alternate embodiment represented by reference 1112', is provided with hooks 1120'. The hooks 1120' are depicted at the electrode end 1112*a*. The hooks 1120' may retract alongside of the electrode outer surface 1112*c*, or within a groove at the end of the electrode (not shown), and deploy upon reaching the chamber space. Alternatively, the hooks 1120' may be provided in conjunction with a sleeve (not shown) having an inner circumference that fits on the electrode end, or in an annular groove provided in the electrode surface (at or near the end of the electrode) in which the circumferential sleeve (to which the hooks 1120' are attached) may reside. The sleeve may be of an elastomeric material or may be molded onto the electrode end, or may be provided using any other installation method. According to some embodiments, when the electrode 1112' reaches the destination, where the electrode 1112' is inserted to the desired depth (e.g., preferably into epicardium, or into the chamber space), the hooks 1120' are released. Preferably, the hooks 1120' secure the electrode against an upward movement or other displacements, and facilitate maintaining the location of the electrode. The hooks 1120', in addition to the spiral turnings of the electrode 1112, therefore further secure the electrode 1112' in position, and aid to maintain the pacemaker, such as the pacemaker 1110 (FIG. 2D), or other pacemakers shown and described herein, in a secure position at the implantation location on the heart (e.g., including after installation, when the second part is connected to the first part). In addition to the electrode spiral implantation, the additional fixation provided by the hooks 1120' may aid to improve the pacing thresholds and sensitivity.

Figure 2F:
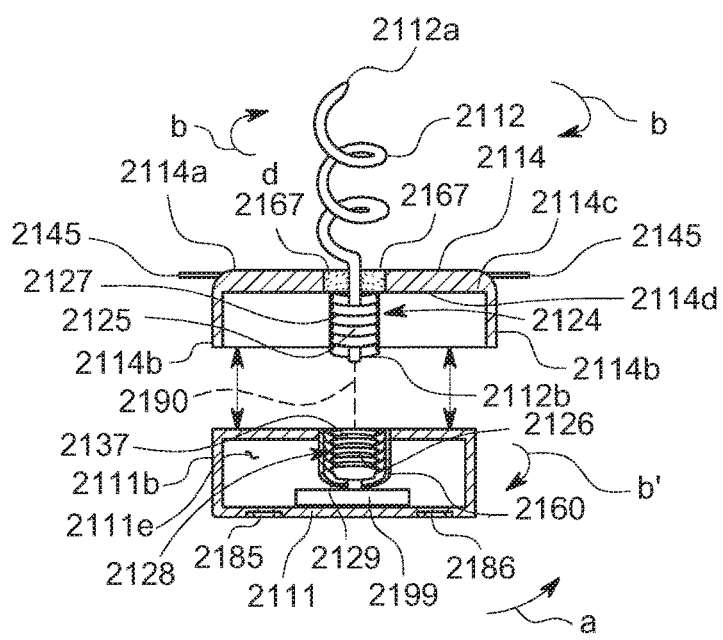
FIG. 2F is a sectional view of an alternate embodiment of a pacemaker according to the invention.

Referring to FIG. 2F, according to an alternate embodiment, a pacemaker 2110 is shown having a configuration similar to the pacemaker 1110, shown and described herein, where the support or cover 2114 makes a threaded connection with the case or bottom 2111, via a threaded connector arrangement. The pacemaker 2110, similar to the pacemaker 1110, is constructed with the top or cover 2114 having a flange 2114*b*. The flange 2114*b* may be circumferential (or another shape) to match the profile of the side wall 2111*b* of the case 2111. In the embodiment depicted in FIG. 2F, the pacemaker 2110 includes a support or cover 2114 that carries the electrode 2112. Preferably, the electrode 2112 is attached to the cover 2114. The cover 2114 includes the flange or cover side wall 2114*b* that is shown extending from the top surface 2114*a*, with the electrode attached thereto or carried thereby. In the pacemaker embodiment illustrated in FIG. 2F, the first part (the cover 2114) is aligned with the second part (case 2111), and the second part 2111 is then fitted into the flange 2114b. (Alternatively, the second part or case 2111 may be configured to receive the flange 2114b.) The alignment of the cover and case parts also aligns the electrode 2112, and preferably, aligns the case connecting electrode end 2112b (shown extending below the top surface 2114a) with a connecting path 2190.

According to some embodiments, the connecting path, such as the path represented by 2190 or portions thereof within the first part and second part, may be sealed with a suitable sealing component (e.g., septum, gasket, or the like), and the connecting path may contain a connector that makes a connection with the case circuitry (through a hermetic seal, which may be through the hermetic case seal) and is connectable to receive or make a connection with the electrode. According to preferred embodiments, the connector may be used to secure together the first part (cover 2114) with the second part (case 2111).

The pacemaker 2110 illustrated in FIG. 2F includes a first connector 2124 shown comprising a first threaded portion 2125 provided on the top or cover 2114, and a second connector comprising a socket 2128 with a second threaded portion 2126 provided on the case or bottom 2111. The first threaded portion 2125 is shown having male threads 2127 thereon which are matingly configured to fit with the female threads 2137 of the second threaded portion 2126 of the case 2111. The second threaded portion 2126 preferably comprises a socket 2128 into which the first connector threaded portion 2125 is received. As shown in FIG. 2F, the electrode end 2112b preferably is provided with the first connector 2124 and makes a connection with the case circuitry via socket 2128, and preferably via a contact 2129 within or configured as part of the socket 2128. The contact 2129 is shown making a connection with the case circuitry 2199. According to preferred embodiments, the second connector or socket 2128 preferably is sealed from the case circuitry with a suitable seal 2160 (e.g., epoxy, silicone or other suitable material), which seal 2160 preferably provides a barrier, electrical insulation, or both. The seal 2160 preferably may provide a hermetically sealed environment for the case circuitry, battery and other case components. The seal 2160 is depicted in FIG. 2F encasing the socket 2128, and sealing the contact 2129, allowing the contact 2129 to make a connection with the electrode end 2112b outside of the sealed case environment 2111e, and make a connection with the case circuitry 2199 that is housed within the sealed case environment 2111e. The seal 2160 preferably seals around the socket 2128 and contact 2129. The case 2111, including the socket 2128, forms a sealed, e.g., hermetically sealed, enclosure for the case components. The cover 2114 preferably may seal the electrode end 2111b, and more preferably a portion thereof, so that at least a portion of the electrode end 2111b is available to make electrical contact with the socket 2128 and more preferably, the contact 2129. According to some embodiments, the contact 2129 may comprise a contact point of a circuit board (e.g., of the circuitry 2199) housed within the case 2111. The connection between the first part (cover 2114) and the second part (case 2111) preferably is made using the connectors 2124, 2128, and preferably the respective matingly provided threads, 2127, 2137. The connectors, such as the connectors 2124, 2128, preferably are insulated as needed to prevent any undesired contact between the electrode 2112 and any surface acting as an anode (such as, for example, a case body or top cover 2114). Alternatively, the connector 2124 may electrically connect the electrode 2112 to the circuitry 2199 by making an electrical connection between the connector threads 2127 and the socket threads 2137 (where the socket 2128 via the threads 2137 is electrically connected to the circuitry 2199).

According to preferred embodiments, the first part (cover 2114) and second part (case 2111) may be connected by rotating the second part 2111 onto the first part 2114. According to preferred embodiments, a rotation orientation is provided. According to a preferred rotation orientation, this may be done by rotating the second part 2111 in a direction indicated by arrow "a" (FIG. 2F), which is shown as a counterclockwise direction, to screw the threaded portion 2126 of the second connector or socket 2128 onto the threaded portion 2125 of the first connector 2124. According to a preferred configuration, the first part (the cover 2114) is attached to the heart by rotation of the cover 2114 and in particular to rotate the electrode 2112 and tip 2112a in the direction of arrow "b", which is shown as a clockwise direction, so that the electrode 2112 spirals into the heart. The second part (case 2111) may be removed from the first part (cover 2114) by rotating the case 2111 in a direction indicated by arrow "b'" which is a rotation that is directionally similar to the rotational direction of attachment of the electrode (i.e., clockwise), when the first part 2114 is installed.

According to some embodiments the connector and/or threads may be constructed from metal, such as titanium, or another suitable material, with suitable insulation for the electrode 2112 (to insulate the electrode from the cover 2114, case 2111, or other anodic contact). Alternatively, the threaded portion 2125 and threads 2127 of the connector 2124 may be constructed from a resin, epoxy, or other suitable biologically compatible material which may also act as an insulator for the portion of the electrode end 2112b that is not designed to make electrical contact with the second connector 2128. Preferably, the electrode 2112 is insulated from the anode portion of the cover 2114, such as the top surface 2114a, or top wall 2114c (and or side wall 2114b), with a suitable insulator 2167. The insulator 2167 may comprise any suitable material that is biocompatible, and which provides a seal between the electrode 2112 and the cover 2114. The seal 2167 may be separate from the connector 2124, or, alternatively, according to some embodiments, may be provided as part of the connector 2124. (According to some embodiments, the seal may be of any suitable dimension, and, according to some embodiments, may comprise a coating provided on the electrode in the area proximal to the top wall 2114c of the cover 2114.) According to some embodiments, the connector or threaded portion 2125 may be constructed from the material that comprises the seal 2167, and provides insulation thereof from the electrode 2112 when connecting with the case 2111. A portion of the electrode, such as the electrode end 2112b (or tip thereof) may be uncovered and available to make contact with the case circuitry (e.g., 2199), even though other portions of the electrode end 2112b are insulated or sealed.

Alternatively, the connector 2124 or threaded portion 2125 may be constructed from a suitable material (including metal) that is insulated from the electrode 2112, and more particularly the electrode end 2112b. The socket 2128 may be constructed from any suitable material, which may include insulators, or a metal, and which preferably is biocompatible. The socket 2128 receives the connector 2124, and preferably the threaded portion 2125 thereof. The socket 2128 or portion thereof, preferably is sealed from the case interior.

Figure 2G:
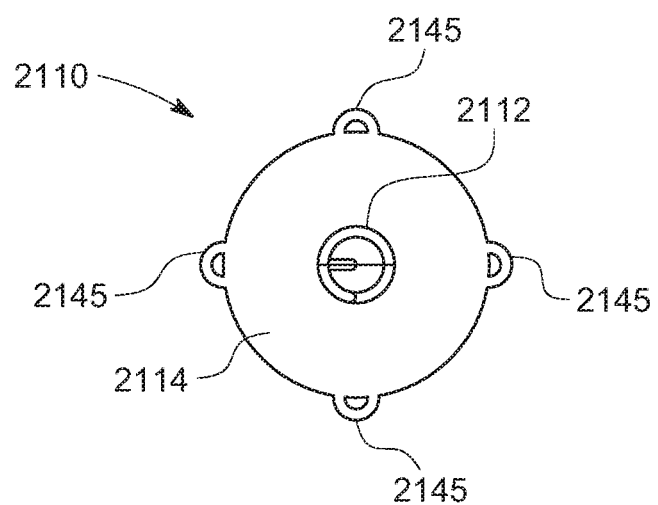
FIG. 2G is a top plan view of the pacemaker of FIG. 2F.
Figure 2H:
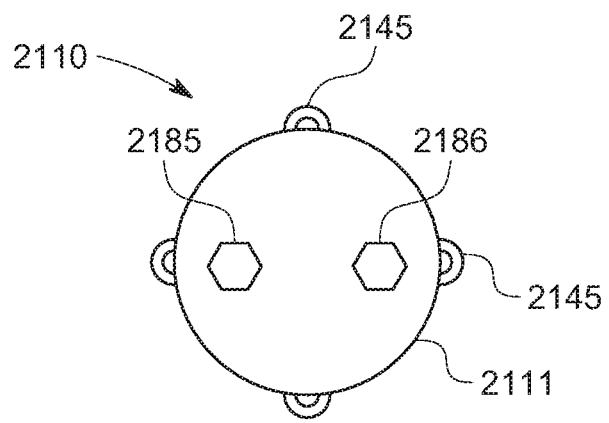
FIG. 2H is a bottom plan view of the pacemaker of FIG. 2F.

Similar to the mounting elements 1145 in FIG. 2D, mounting elements 2145 and provided in FIG. 2F, preferably at the top of the cover 2114. The mounting elements also are illustrated in FIGS. 2G and 2H.

Figure 2I:
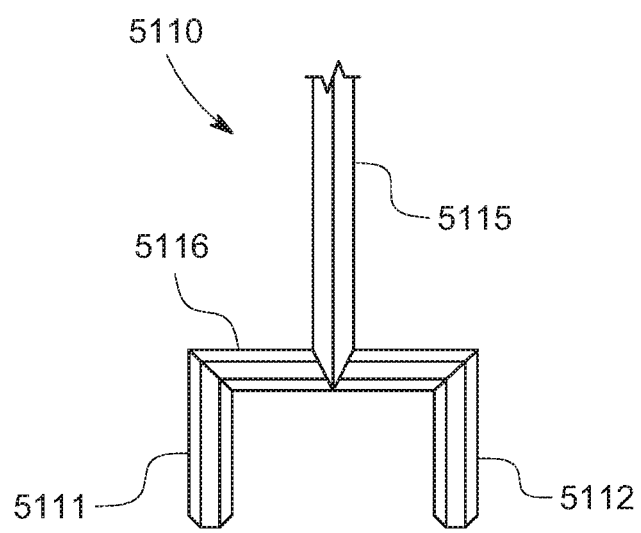
FIG. 2I is a perspective view of a tool for connecting and/or disconnecting the pacemaker parts.
Figure 2J:
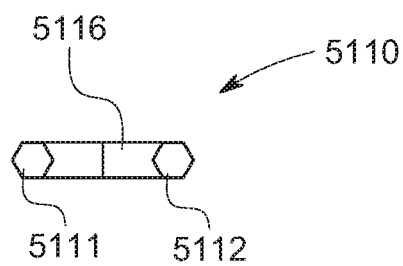
FIG. 2J is a bottom plan view of the tool of FIG. 2I.
Figure 2K:
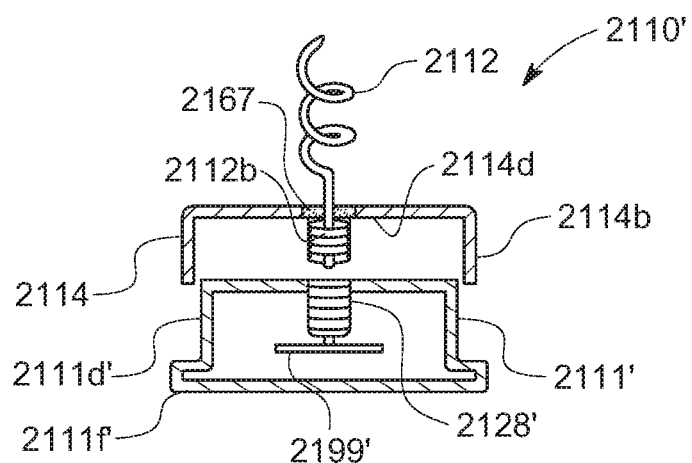
FIG. 2K is a further sectional view of the pacemaker of FIG. 2F, shown with an alternate base configuration.

An alternate embodiment of a pacemaker 2110' is shown in FIG. 2K which is similar to the multi-component pacemakers 1110 and 2110, but is shown having a case 2111' with an annular step or wall portion 2111d' that is smaller in diameter than the distal end 2111f'. The annular recessed or smaller diameter wall 2111d' is provided to accommodate the flange 2114b of the cover 2114, when the second part or base 2111' is connected with the top part or cover 2114. Although not shown, the case circuitry and connectors of the pacemaker 2110' may be provided similar to those shown in the embodiment depicted in FIG. 2F (or other figures). A case connector is represented by reference 2128' and may be similar to the connector 2128 shown and described in FIG. 2F (or other connector). The case geometry illustrated in FIG. 2K may be applied for use in the other embodiments.

Figure 2L:
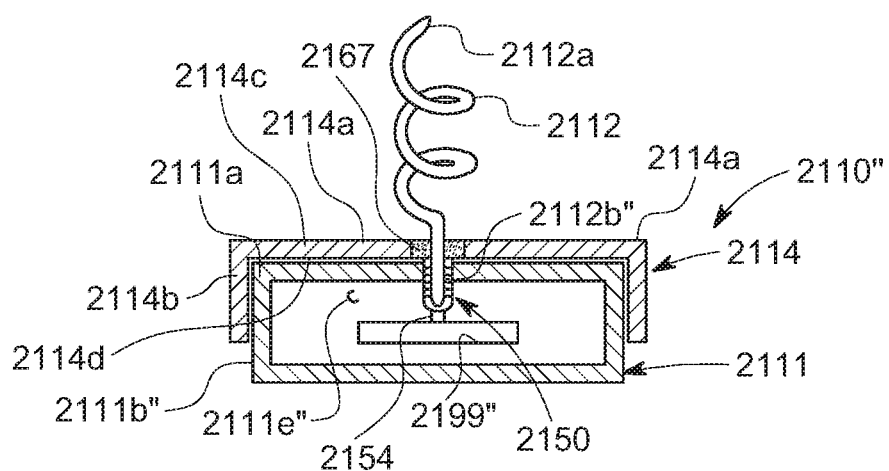
FIG. 2L is a sectional view of an exemplary depiction of the pacemaker of FIG. 2F, shown with another exemplary embodiment of an alternate connector for connecting the electrode with the case circuitry.

Referring to FIG. 2L, an alternate embodiment of a connector is illustrated in conjunction with a pacemaker. The connector of FIG. 2L is an example of a connector that may be used in conjunction with the multi-part pacemakers shown and described herein. The pacemaker 2110" is shown in FIG. 2L and is similar to the pacemaker of FIG. 2F, but includes an alternate connecting mechanism to connect the electrode 2112 with the case circuitry 2199". The pacemaker 2110" is shown having a case 2111" with a side wall 2111b". The electrode, such as the electrode 2112, and in particular the electrode end, such as the end 2112b", is shown connecting with the circuitry 2199" (FIG. 2L). In FIG. 2L an electrode guide 2150 is shown provided in the case 2111" for receiving the electrode 2112b" therein. The electrode guide 2150 preferably includes an electrical connection 2154 to connect the electrode 2112 with the case circuitry 2199"

According to some preferred embodiments, when the first part (support or cover, e.g., 1114, 2114) and the second part (case 1111, 2111, 2111', 2111") are connected together, the electrode, e.g., 1112, 2112 via the electrode connecting end 1112b, 2112b, 2112b" makes a connection with the case circuitry 1199, 2199, 2199" from the electrode portion which, in the depiction illustrated, is located on the interior side of the cover or top (see, e.g., 2114d in FIG. 2F and in FIG. 2L). The top surface 1114a, 2114a of the top or cover 1114, 2114 rests on the surface of the endocardium when the pacemaker (e.g., 1110, 2110, 2110', 2110", 2110'") is implanted on the heart (and preferably when the first part is implanted).

Figure 2M:
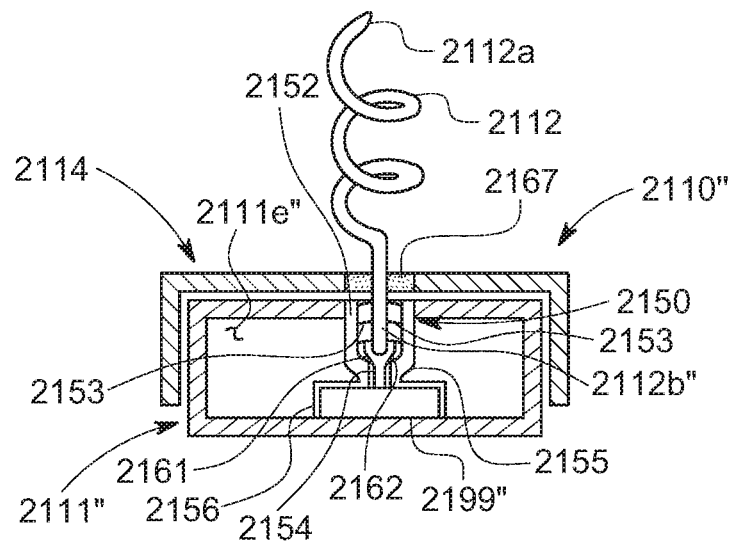
FIG. 2M is a enlarged sectional view of the pacemaker of FIG. 2L.
Figure 2N:
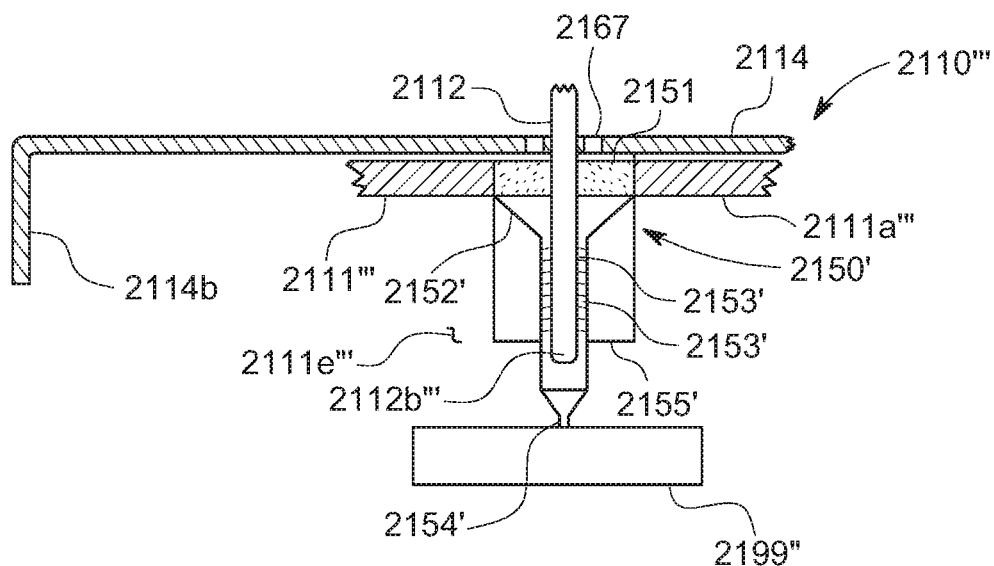
FIG. 2N is another enlarged sectional view of an exemplary depiction of a connector for connecting the electrode with the case circuitry, where the case and cover are represented in partial views.

As depicted in some exemplary embodiments, such as for example in FIG. 2N, alternatively, the electrode end 2112b'" may extend beyond the flange 2114b so that the electrode end 2112b" may enter an electrode guide 2150' of the case top 2111a'", and then guide the connection of the second part or base 2111'" to be received within the flange 2114b. Conversely, according to alternate embodiments, the cover flange or sidewall 2114b may be received within the case 2111 (e.g., the case side wall 2111b), and in these embodiments, the case side wall preferably is slightly wider than the cover flange.

In the embodiments illustrated, the case 1111, 2111 (and 3111, 4111) has a sealed environment, and may hermetically seal the case connector area at one or more locations, so that the electrode connector of the case (the connector that connects with the electrode end 1112b, 2111b, such as, for example, the socket 2128, or connector 1130, 2150) is outside of the hermetically sealed area (see e.g., 2111e", FIGS. 2L and 2M) of the case 1111, 2111, 2111', 2111". The exemplary embodiments depicted in FIGS. 2L, 2M and 2N, illustrate exemplary connection mechanisms for connecting the first and second parts. Other suitable means for connecting the first part and second part together, to make electrical contact between the electrode 1112 (or 2112) and circuitry housed within the case, may be employed.

According to an exemplary depiction, a connector 2150 is shown in FIGS. 2L and 2M and a connector 2150' in FIG. 2N, representing a connection between the electrode 2112 and the case circuitry 2199". The connector system is shown comprising an entry path for receiving the electrode, such as the electrode 2112, and in particular the electrode end 2112b" (FIGS. 2L and 2M) and 2112b'" (FIG. 2N). As illustrated in the larger view of FIG. 2N, the entry path may comprise a septum 2151, which may comprise a suitable sterilizable material through which the electrode 2112b" or 2112b'" may pass or puncture. The septum 2151 preferably also electrically insulates the electrode 2112 from contact with the case top wall 2111a'". The connector guide 2152' is depicted in the enlarged view of FIG. 2N, and is shown having a tapered configuration, and may be provided to receive the electrode end 2112b" once the electrode end passes the septum 2151. The guide or connector 2152 (FIG. 2M), 2152' (FIG. 2N) may be electrically connected with the case circuitry, schematically represented by the box 2199". The guide 2152, 2152' may comprise one or more engaging elements, such as the fingers 2153, 2153" which may be biased to the electrode path (i.e., inwardly) to make contact with the electrode 2112b', 2112b", respectively. Although the fingers 2153, 2153' are shown, a sleeve or other suitable component may be used to contact the electrode 2112b', 2112b". The fingers 2153, 2153' may electrically connect the electrode 2112 with the case circuitry, directly or through a wired connection (e.g., see 2154, FIGS. 2M and 2154' FIG. 2N). Referring to FIG. 2M, an example of a connection is shown, depicting electrical conduits, such as wires 2161, 2162, which are used to electrically connect a contact element that contacts the electrode 2112b, such as the fingers 2153, with the circuitry 2199". In the embodiments illustrated, the connector, such as the connector 2150, 2150', may comprise or be housed within a chamber 2155 (see FIG. 2N) that is hermetically sealed from the case interior 2111e" (FIGS. L and M) and 2111e'" (FIG. 2N). The chamber 2155 (FIG. 2M), 2155' (FIG. 2N) may house the connector 2150, 2150' and connecting components, so that the electrical connection with the electrode 2112 is made, but there is no penetration by the electrode 2112 into the hermetically sealed case environment 2111e". The pacemaker 2110" shown in FIG. M, is depicted to show an example of the sealing of the circuitry 2199" and connector 2150, where a seal represented by the seal 2156 is illustrated. For example, as depicted in FIG. 2M, the seal 2156 may seal the circuitry 2199". The seal 2156 may be provided to seal the circuitry 2199" as well as the connector and interior case space (see, e.g., 2111e" in FIG. 2M), to seal the components within the case (e.g., pacing circuitry, power supply, etc.). While shown in the embodiment of FIG. 2M, the sealing may be provided for the other pacemaker embodiments.

Figure 2O:
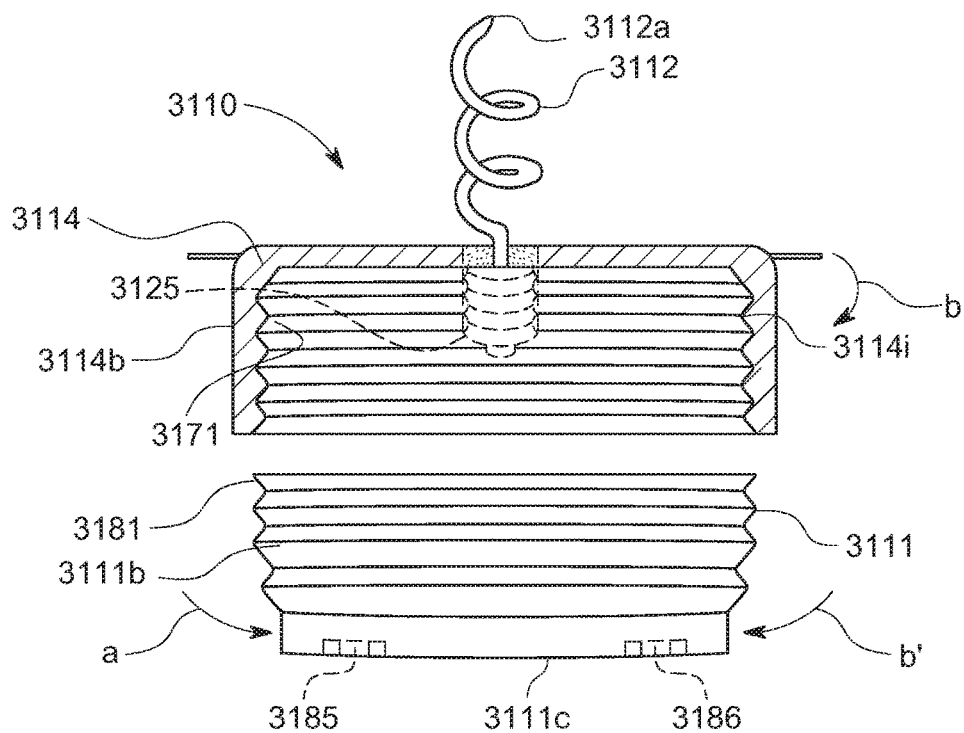
FIG. 2O is a front view of a multi-part pacemaker shown with an alternate connecting element comprising threaded portions, with the first pacemaker part shown in sectional view, and the second pacemaker part shown in an full view.
Figure 2P:
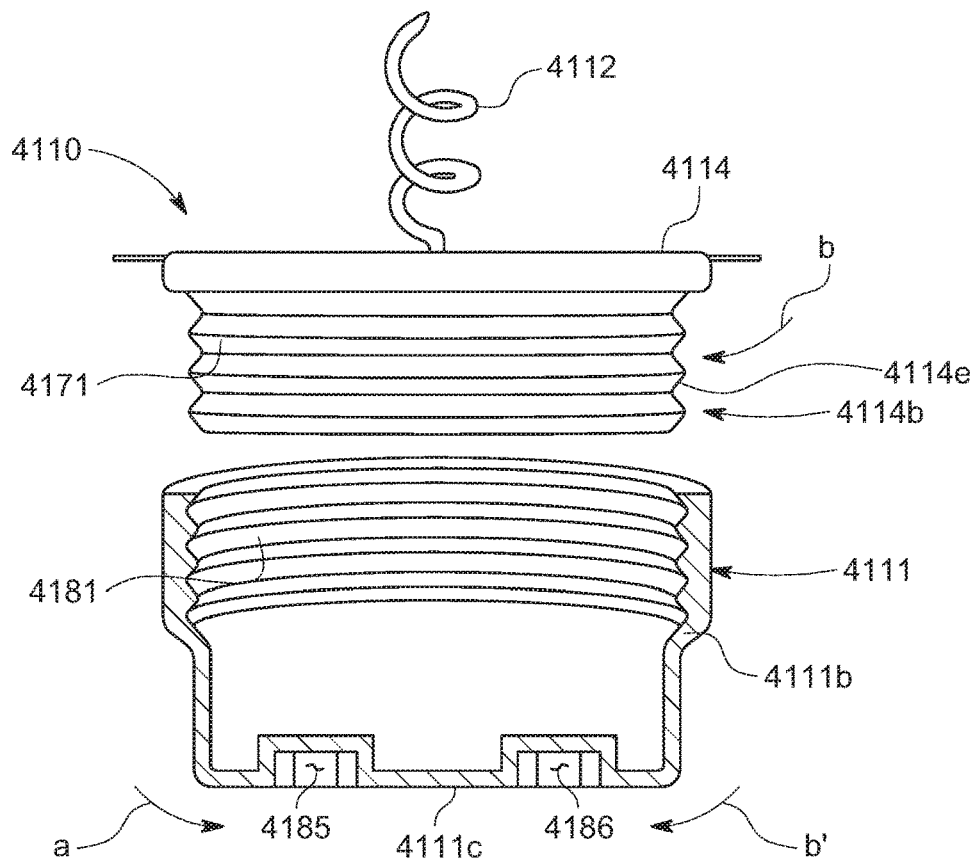
FIG. 2P is a front view of a multi-part pacemaker shown with another alternate connecting element comprising threaded portions, with the first pacemaker part shown in an elevation view, and the second pacemaker part shown in a sectional view.

Additional examples of connections between the first part and the second part are illustrated in FIGS. 2O and 2P. Referring to FIG. 2O, a pacemaker 3110 is shown having a first part shown comprising a top 3114, and a second part shown comprising a case or bottom 3111. The first part 3114 and second part 3111 may be constructed similar to the pacemaker parts of the pacemakers shown and described herein (such as those pacemakers 1110, 2110 and 2110', 2110", 2110'"). The pacemaker 3110 includes threads to connect the first part 3114 and second part 3111. In the exemplary depiction illustrated, the pacemaker 3110 is shown having a first part 3114 with threads 3171 formed on the interior wall 3114*i* of the flange 3114*b*. The threads 3171 are shown as male threads. The second part or case 3111 is shown having threads 3181 which are disposed on the exterior of the side wall 3111*b*. The threads 3181 preferably are mating threads that mate with the threads 3171 of the cover 3114. In the illustration depicted, the threads 3171 preferably are configured as female threads to comprise a socket, while the case threads 3181 are shown comprising male threads that fit within the female threads 3171 or socket. The rotation of the case 3111 preferably secures the second part or case 3111 to the cover 3114, and may be connected when the cover 3114 (and its electrode 3112) is implanted (e.g., at the heart site via the electrode tip 3112*a*). According to a preferred configuration, the threads 3171 of the first part 3114 preferably are configured to receive the second part 3111, for attachment to the first part, by rotating the second part in a rotational direction (arrow a) that is opposite the rotational direction that the first part is rotated to implant the electrode 3112 of the first part into the heart (arrow b). Conversely, removal of the second part 3111 from the first part 3114 preferably is accomplished by rotating the second part in a rotational direction that is the same rotational direction (arrow b') as the rotational direction that the first part 3114 is rotated (arrow b) to implant the electrode 3112 into the heart. The threaded connection arrangement preferably provides this capability. Preferably, the bottom wall or surface 3111*c* of the case 3111 is configured with a structure to permit a tool to rotate it, such as, for example, the bores 3185, 3186, or other suitable structure for allowing a tool to grasp the case 3111 and rotate it to connect it to the first part or cover 3114 (when the case 3111 is being implanted at the implant site). See e.g., the tool 5110 shown in FIGS. 2I and 2J. In the exemplary embodiment of FIG. 2O, there is illustrated a connector 3125 for connecting the electrode 3112 to the case circuitry (such as case circuitry shown and described herein in connection with the other figures and descriptions herein). The connector 3125 shown may comprise threads or other suitable connector (such as any of the connectors in FIGS. 2D-2N).

Referring to FIG. 2P, a multi-part pacemaker 4110 is shown having a first part or cover 4114, and a second part or case 4111. The first part shown comprising a top 4114, and a second part shown comprising a case or bottom 4111. The first part 4114 and second part 4111 may be constructed similar to the pacemaker parts of the pacemakers 1110 and 2110 shown and described herein, but include threads to connect the first part 4114 and second part 4111. In the exemplary depiction illustrated, the pacemaker 4110 is shown having a first part 4114 with threads 4171 formed on the exterior wall 4114*e* of the flange 4114*b*. The threads 4171 are shown as male threads. The second part or case 4111 is shown with threads 4181 which are disposed on the interior of the side wall 4111*b*. The threads 4181 preferably are mating threads that mate with the threads 4171 of the cover 4114. In the illustration depicted, the threads 4181 of the second part 4111 preferably are configured as female threads to comprise a socket, while the cover threads 4171 are shown comprising male threads that fit within the female threads 4181 or socket. The rotation of the case 4111 preferably secures the second part or case 4111 to the cover 4114, and, according to preferred implementations, may be connected to the cover 4114 when the cover 4114 is already installed at the heart installation site (via implantation of the cover electrode 4112). According to a preferred configuration, the threads 4181 of the second part 4111 preferably are configured to fit onto the first part threads 4171, by rotating the second part 4111 in a direction (indicated by arrow a) which is opposite the rotational direction that the first part 4114 is rotated to implant the electrode 4112 of the first part into the heart. Conversely, removal of the second part 4111 from the first part 4114 preferably is accomplished by rotating the second part 4111 in a rotational direction that is the same rotational direction (arrow b') as the rotational direction that the first part 4114 is rotated (arrow b) to implant the electrode 4112 into the heart. The threaded connection arrangement preferably provides this capability. Preferably, the case 4111 is configured with a structure to permit a tool to rotate it, such as, for example, the bores 4185, 4186 disposed in the case bottom wall 4111*c*, or other suitable structure, for allowing a tool to grasp the case 4111 and rotate it to connect it to the first part or cover 4114 (when the case 4111 is being implanted at the implant site). The pacemaker case parts 3111, 4111 shown respectively in the exemplary embodiments in FIGS. 2O and 2P, may be removed from a respective cover 3114, 4114 after the pacemaker 3110, 4110 has been implanted at the site. This permits one to change out the case part 3111, 4111, respectively, with the same (replacing), or with a new (replacement case part), while leaving the cover part 3114, 4114, and its electrode 3112, 4112 installed at the site. The pacemaker 4110 of FIG. 2P preferably includes the circuitry as shown and described herein in conjunction with the pacemakers of other embodiments, and the electrode 4112 preferably connects with case circuitry.

The threaded means for connecting the first pacemaker part to a second pacemaker part, as illustrated in the embodiments of FIGS. 2O and 2P, may be employed as a connection mechanism to connect the other pacemaker parts shown and described herein (e.g., such as the pacemakers shown and described in FIGS. 2D through 2N).

In addition, the embodiments herein may separate the electrode 2112 (and electrode 1112, 3112, 4112 in the other embodiments illustrated) from electrical contact with the top or cover. This may be done with an insulator (i.e., electrical insulator), or coating provided where the electrode 1112, 2112, 3112, 4112 passes through the cover (1114, 2114, 3114, 4114). The cases shown and described herein may be provided with a keyed configuration or surface to permit a tool to be used to manipulate the case to connect the case to the cover. According to a preferred embodiment, a tool 5110 is illustrated in FIGS. 2I and 2J that includes a pair of legs 5111, 5112, which are configured to fit within the bores (see e.g., bores 2185, 2186 of FIGS. 2F and 2H, bores 3185, 3186 of FIG. 2O, and bores 4185, 4186 of FIG. 2P) respectively, provided in the bottom wall of a case 1111, 2111, 3111, 4111. The tool 5110 is shown having a handle 5115, and a yoke that connects the legs 5111, 5112. The cross sectional profile of the legs 5111, 5112 (or leg ends), preferably matches the profiles of the respective bores, and, is slightly smaller than the bore profile, so that the legs 5111, 5112, or portion thereof (e.g., leg ends), fit within the respective bores. The handle 5115 preferably is connected with or manipulated by a thoracoscope or thoracoscopic tool, which carries the tool 5110 or is configured with the tool ends and/or legs 5111, 5112, so that the tool 5110 and/or tool end 5111, 5112 may be rotated to rotate the case or second part relative to the first part or cover (or to rotate the pacemaker parts together if the pacemaker is being implanted in an already assembled together condition). In the exemplary depiction, the tool legs 5111, 5112, and bores are hexagonal shape, but could be other suitable shapes.

Although shown and described in connection with the pacemaker 2110, the two-part pacemakers of the invention, such as the pacemaker 1110, may employ a connection mechanism like that illustrated in FIGS. 2L, 2M, and 2N, or FIG. 2O or 2P, or may employ another suitable connection mechanism. In addition, the pacemaker circuitry may be configured to operate with the receivers shown and described herein, and/or energy harvesting features that capture the heart kinematic energy and convert it to electrical energy for use in carrying out the pacemaker and/or receiver functions.

According to alternate embodiments, the pacemakers 1110, 2110, 2110', 2110", 2110''', 3110, 4110, like other pacemakers shown and described herein (e.g., 110, 310), may be configured with an energy harvesting feature. For example, according to some alternate embodiments, the energy harvesting feature may comprise an optional energy harvesting circuit within the case 1111, 2111, 2111', 2111", 3111, 4111, such as for example, the MEMS discussed herein, or any other suitable harvesting component that converts the heart kinematic motion into electrical energy. The electrical circuitry may convert the kinematic energy, and store or make available the energy (e.g., in the battery circuit, capacitor, or other form), for use to power the functions of the pacemaker 1110, 2110, 2110', 2110", 2110''', 3110, 4110 as well as associated receivers in the arrangements depicted. 1001451A method, system and devices for carrying out multi-sensing detecting and pacing operations are provided. According to an alternate embodiment, features of the device include multi-sensing operations. The devices and system provided for multi-sensing and pacing at locations of the heart may include the energy conversion feature or MEMS, or may be provided without the energy harvesting functionality. FIGS. 4, 5, 6 and 7, depict a multi-sensing operation where a heart 300 is represented schematically. A number of sensing points are shown provided at locations of the heart 300.

The present method, system and devices provide improved stimulation of the heart through directed movements. Embodiments of the method, system, and devices, recreate the spiral movement of the heart, and preferably recreate the spiral movement at least in one layer of myocardium. The method, system and devices are configured to produce the spiral movement in at least one layer, such as the myocardium, which also imparts a directional movement to pull the other layers to move in the correct way. The receivers and desired movement may be configured based on the condition being treated or remediated.

Embodiments of the method, system and devices involve providing receivers, which are placed epicardially. According to embodiments, the receivers include a mounting portion or element, and the receivers are attached to the heart (preferably with the mounting portion or element). In an exemplary embodiment, the receivers mounting portion is configured to pierce the heart tissue, and may be configured having a spiral shape. For example, the receiver may be screwed into the myocardium, a suitable penetration depth to secure the receiver thereon. For example, the receiver may be screwed in deep enough to secure itself and deliver appropriate impulses (which is some implementations, for example, may be about 10 mm into the myocardium). Surgical instruments may be used to place the receivers at the locations on the heart. According to an exemplary implementation, the placement of the receivers may be carried out using thoracoscopy, such as, for example, by insertion of a thin, flexible tube (e.g., a thoracoscope), through a small incision in the patient's chest. According to some embodiments, the tube may be configured with fiber optic cables that allow visual inspection of the implantation site. In addition, or alternatively, one or more tubes of, or associated with, the thoracoscope also may be used for the insertion, placement and mounting of receivers.

The receivers pace the myocardium in order that is dictated by the pacemaker that the body of the pacemaker will dictate. The receivers receive a signal from the pacemaker and associated circuitry that electrically connect therewith. According to some preferred implementations, the electrical connection comprises a wireless connection, and the receivers receive the information wirelessly (such as, for example, through radio waves). The radio waves may be generated by a transceiver or transmitter provided in the pacemaker. The transmitter or transceiver may be disposed within, or coupled to, the pacemaker circuitry. The receivers are configured at locations on the heart to produce signals to stimulate the heart muscle to provide pacing. The receivers are configured so that they will pace the myocardium in the desired sequence or arrangement. Preferably, the receivers are configured to pace the heart to effect contractions of the heart to simulate the normal heart contraction function, by effecting contractions that occur spirally from the apex toward the base. According to a first preferred pacing arrangement, the receivers are configured to pace the myocardium consecutively, from the apex toward the base of the heart. According to another preferred pacing arrangement, the receivers are configured to pace the myocardium simultaneously. The most important that they will then pace myocardium either consecutively from apex toward the base of the heart or simultaneously if we will not be able to provide the consecutive action. The system, method and devices are designed to impart stimulus so the heart will contract spirally from apex toward the base as it happens naturally. Embodiments may be implemented by providing one receiver that remains on the right atrium appendage which may have a shorter mounting element (for example, the longevity of the spiral mounting part may be about 5-6 mm, as the wall of the right atrium much thinner). The right atrium receiver makes right atrial appendage stimulation on demand, as it happens in regular modern cardiac pacemakers (AAI/R, DDD/R modes). Each receiver preferably may be provided with an electrode that is a desired length, and receiver electrodes may be different in length, as needed for the specific condition being addressed, or heart location to which the receiver will be fixed, and/or where the electrode is desired to extent to. The length of the receiver electrode also may depend on physiology (e.g., adult versus a child, atrial versus ventricular placement, size of the heart, and the like).

According to some embodiments, the receivers are configured to generate their own power needs, so that the receivers may deliver an electrical impulse to the heart at the respective locations at which the receivers are installed on the heart. The receivers preferably include an energy generation circuit or circuitry, which preferably includes components that generate the power needs of the receiver (e.g., for generating and delivering an electrical impulse, and/or sensing and transmitting a signal of sensed information, such as, of heart activity). According to some preferred embodiments, the circuitry includes means for converting an electrical signal (which, for example, may be an RF signal generated by another component) to electrical energy. The means may include a transducer and capacitor, or circuitry in which these components are arranged. According to some embodiments, the transducer may receive waves, such as radio frequency (or RF waves), and the circuitry via the capacitor converts the radio or acoustic waves to electrical energy. According to some embodiments, the electrical energy may be stored until needed, which in this case, would be until the receiver is triggered to deliver an electrical impulse. Alternatively, the RF energy may be released from a source as a trigger, so that the actuation of the receiver to deliver an electrical impulse is implemented upon receipt of the RF signal by the receiver. In these latter embodiments, the receiver circuitry may include a trigger switch, that functions to deliver or cause delivery of the impulse from the receiver (to the heart) when the triggering signal (RF frequency or other acoustic signal) is received by the receiver). Though referred to as an RF signal in accordance with preferred embodiments, it may comprise acoustic energy or an acoustic wave. According to some embodiments, the receiver also includes one or more chips that are configured with instructions (e.g., logic), to regulate the operation (discharge) of the electrical impulse from the receiver, as well as to detect and transmit signals corresponding to the heart operations, such as heart contractions sensed at the receiver location (which may, for example, include heart pulse, pulse duration, pulse intensity, and the like). Some embodiments provide signal generating circuitry within the pacemaker (such as the pacemaker that is placed at the apex of the heart). The pacemaker may be configured with logic to issue signals to communicate to one or more of the receivers to actuate (and deliver an electrical impulse). The pacing circuitry may include software containing instructions to regulate the impulses delivered from each of the respective receivers, including whether to deliver an impulse at the receiver location, and the order of the impulses, such as whether the receivers should deliver impulses consecutively, or whether a receiver should deliver an impulse to correlate with heart activity at another receiver location. For example, where the sensor information reported by the receivers and receiver and processed by the pacing circuitry (such as by the pacemaker circuitry) determines that an electrical impulse is required at a particular receiver, then that receiver may be actuated apart from other receivers. According to some implementations, the pacing circuitry may actuate the receivers so that the heart contractions take place in accordance with a desired arrangement, for example, to contact the heart in a spiral and upward direction to replicate the natural contractions of a normally functioning heart.

For example, the receiver arrangements and order of their operation, as well as the intensity of the electrical impulse to deliver, and the frequency of the impulse delivery, in some instances, may be predetermined based on examinations of the heart, the injection fraction observed versus the desired parameter.

Imaging also may be used prior to or during the placement of the receivers. For example, the pacemaker pacing circuitry preferably includes configurable settings that permit the voltage delivered by the receivers and pacemaker to be regulated. According to some implementations, threshold values may be set as a trigger for one or more of the receiver locations, so that sensed based impulse delivery may be carried out. In some instances, the threshold value may be a voltage value for delivery of the impulse, which may be set in millivolts (mV). The pacemaker, typically installed at the heart apex, and the receivers arranged at different locations on the heart, may be set to deliver a predetermined voltage when actuated to deliver the electrical impulse. The voltage of the impulse may be set in accordance with generally acceptable cardiology procedures. For example, according to some procedures, the impulse delivered to the heart may be larger (e.g., on the order of 2-3 times greater) than the minimum required to induce action in the heart at the impulse delivery location.

The devices according to the invention may be implanted in accordance with general medical procedures. For example, a pacemaker, when installed at the apex of the heart may be positioned, and/or sutured, by making a small incision below the rib cage to provide access to the apex of the heart. Alternatively, thoracoscopy may be used to implant the pacemaker. Typically, one or more lumens may be inserted from outside the body to the placement location, which may include a camera and light, as well as placement tools. For example, forceps may be provided at the end of a guide threaded through a lumen for holding the pacemaker and maneuvering it to the installation site (on the heart). The forceps end may hold the pacemaker until it is installed. Another instrument, such as a suturing tool, may be inserted through the lumen, or inserted through an opening to reach the heart location and be operated to suture the pacemaker in position.

The receivers preferably are implanted onto the heart epicardium using thoracoscopy.

The receivers may, as part of the circuitry, include a chip containing embedded logic. For example, embodiments of the receiver may include a processing component, such as a microprocessor, microcontroller or other suitable processor, and may include software containing instructions for processing signals received by the receiver, such as, for example, an actuation signal (e.g., RF signal or acoustic signal), and/or for processing the signal to actuate the impulse delivery from the receiver. According to some embodiments, the receiver circuitry may be powered by a power generation circuit or chip, that utilizes the energy RF or acoustic energy and converts that into electrical energy and stores that energy (through a capacitor or other component(s)). The acoustic waves or RF energy that the receivers may use to generate or convert to electrical energy may be generated by a separate device, and preferably the pacemaker. As an alternative option, some receivers may be configured with a small battery that may be recharged by the conversion of the RF or acoustic waves.

The system is able to utilize the pacemaker or pacing circuitry to obtain the results of the implementation of the receivers and the effect of pacing the heart at the desired locations. With the present system, the receivers may be positioned and installed at locations of the heart to maximize the pacing activity desired. The positioning of the receivers and sequencing of the electrical impulse delivery of the receivers at the respective heart locations may be controlled. For example, evaluation of the cardiological information, such as, for example, the injection fraction, may be determined and monitored so that the suitable or optimal pacing is implemented to treat the condition. For example, the receivers preferably are located as far apart from each other about the heart, and more preferably to create an electrical loop around the heart. The receivers may be programmed and reprogrammed to pace at the same time, or to pace consecutively (e.g., one after another). The circuitry preferably is addressable through a computer or other link, which preferably may communicate with the pacing circuitry to set or change parameters. The parameters may include parameters relating to the receivers and their operation (such as timing, frequency, pacing order, thresholds for actuation, impulse level (millivolts), and other settings).

Figure 9:
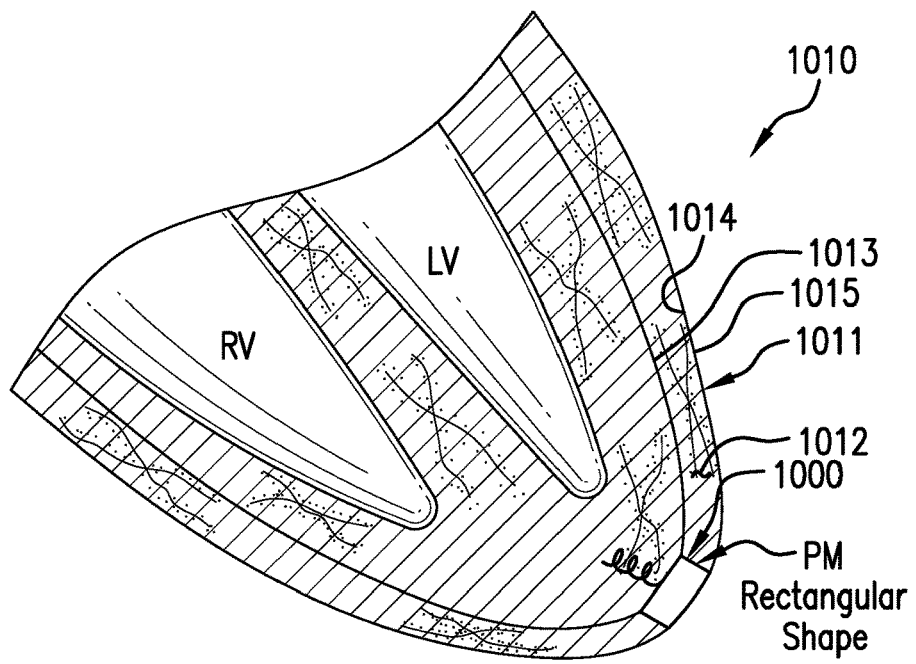
FIG. 9 is a sectional view of an illustration representing a heart, showing a rectangular shape pacemaker disposed between the pericardium and the myocardium.
Figure 10:
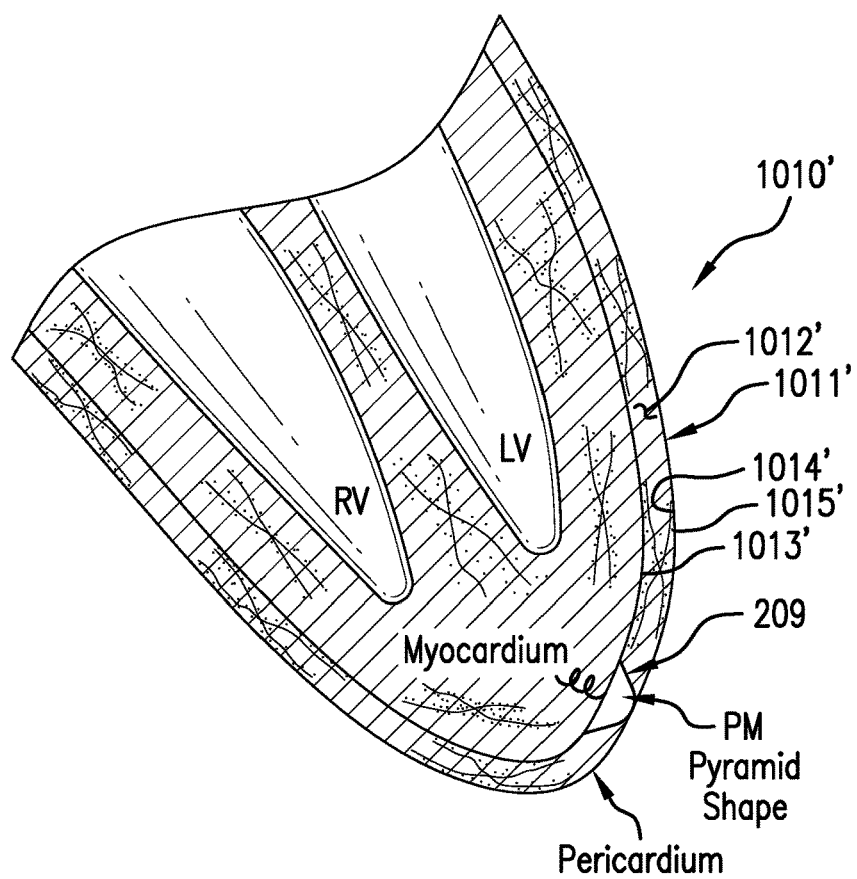
FIG. 10 is a sectional view of an illustration representing a heart, showing a pacemaker configured in accordance with an embodiment of the invention, disposed between the pericardium and the myocardium.

FIGS. 9 and 10 show a heart 1010, 1010', to illustrate the pericardium 1011, 1011', respectively. The pericardium 1011, 1011', respectively, covers the heart 1010, 1010' respectively, and is a tough double layered fibroserous sac. The pericardial cavity 1012, 1012' is shown in the FIGS. 9, and 10. The pericardial cavity 1012, 1012', is shown as a space between the two layers of serous pericardium 1013, 1014, and 1013', 1014', respectively, and is filled with serous fluid. The fluid is designed to protect the heart 1010, 1010' from abrupt external movements or shock. The pericardial sac has two layers, the outermost fibrous pericardium 1015, 1015', and the inner serous pericardium 1013, 1013'.

As shown in FIG. 9, the prior art type rectangular pacemaker 1000 has sharper edges. The pacemaker 1000 and the edges agitates the pericardium when the pacemaker 1000 undergoes movement (such a, for example, movement of the individual, or movement of the heart (pulses or heart contractions). The pacemaker 1000 shown in FIG. 9, is very likely to experience strong rubbing against the pericardium, thereby causing inflammation. The inflammation is further aggravated due to the continuous rubbing of the pacemaker 1000 at the inflamed site (as the pacemaker 1000 is installed at that location on the heart, where it makes essentially the same contact points with the pericardium).

As shown in FIG. 10, the pacemaker 209 is configured as a pyramidal like shape with softened edges and a soft apex. The pacemaker 209 may be provided with the similar components described in connection with the pacemakers shown and described herein (including for example, the pacemakers 110, 110', 110", 150, 310, 1110, 2110, 2110', 3110,4110), and according to some embodiments, may be used with the receivers and other components shown and described herein. The pacemaker 209 preferably may have a deformed pyramid shape with a shortened apex height, and with softened or rounded edges. Alternatively, the pyramidal like pacemaker may have softened edges and a softened apex forming an elliptical or ovoid type shape or profile. The pacemaker 209 of FIG. 10 is shown having a configuration with rounded or softened edges (or with no discrete edges) that results in contact between the pacemaker and the pericardium being smooth contact. Friction and intrusion into the surrounding tissue and layers, such as the outer serous pericardium 1015' (FIG. 10), and the inner serous pericardium 1013', is reduced or eliminated due to the engaged pacemaker surfaces being softened or rounded (or eliminated in their entirety). When the pacemaker 209 rubs against the pericardium (e.g., 1011', and 1013', 1015') the engagement is smooth rubbing, and minimizes or prevents the inflammation and the continuous aggravation of the inflamed tissue (pericardium).

The pacemaker preferably is a solid structure where the pacemaker has a battery inside, micro-schema and MEMS inside. The electrode (cathode) soldered to the body and the body itself serves as a referent part (anode).

Some embodiments may include an energy harvesting feature. In such embodiments, the kinematic energy of the heart movements is harvested and transformed into the electrical energy. The transformed electrical energy is utilized for pacing. According to some preferred embodiments, the energy harvesting and transformation preferably may be done using a MEMS.

Figure 4:
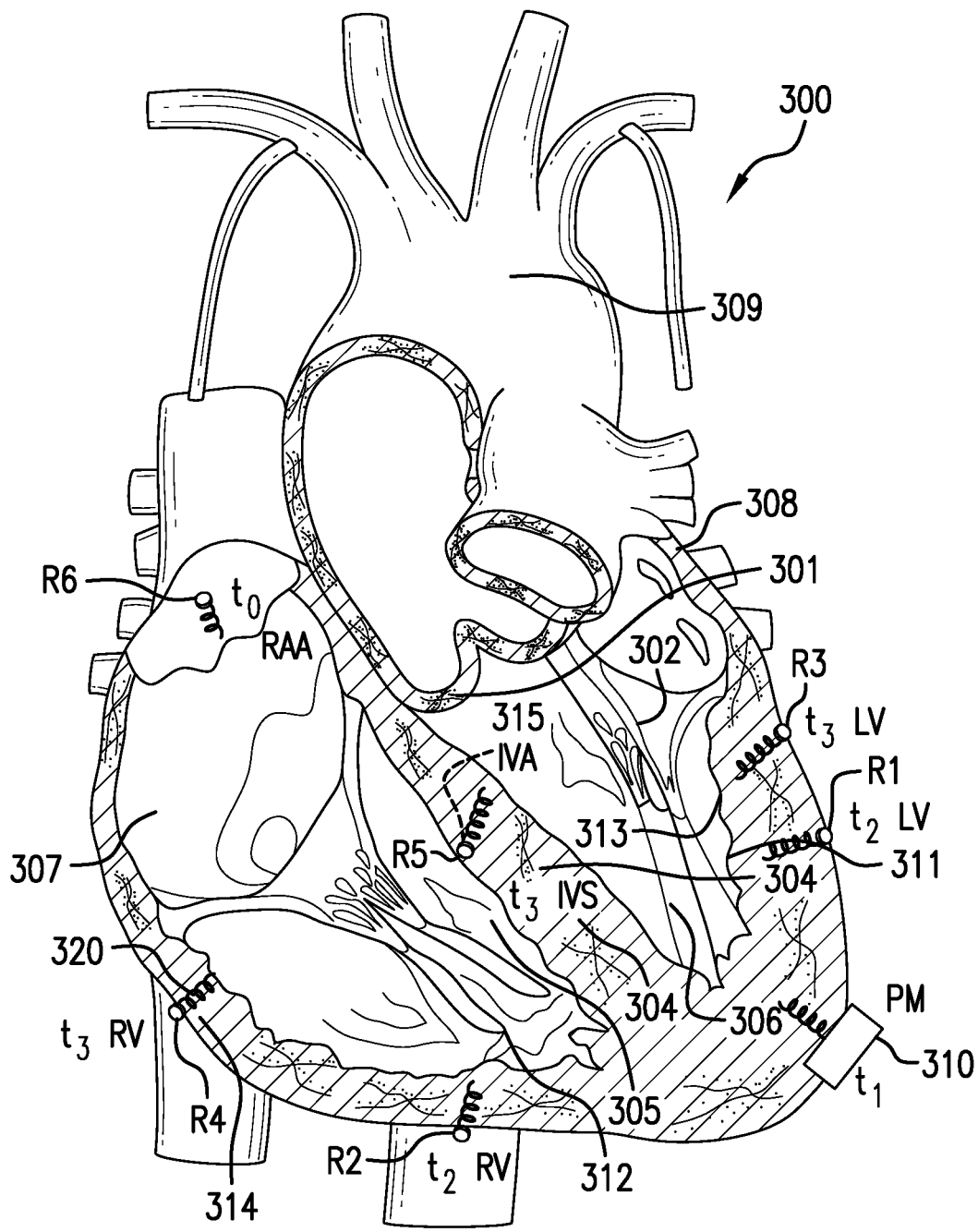
FIG. 4 is a schematic representation of a heart, shown in a sectional view, where a system for conducting multi-sensing and pacing operations of a heart.

A preferred implementation of the devices and system for multi-pacing locations of the heart is depicted in the illustrations set forth in FIGS. 4, 5, 6, 7 and 8. Referring to FIG. 4, a schematic diagram of a heart 300 is depicted in a sectional view, showing the aortic valve 301, the mitral (or bicuspid) valve 302, and the tricuspid valve 303. The ventricular septum 304 divides the right ventricle 305 from the left ventricle 306. The right atrium 307 and left atrium 308 are shown, with the aorta 309 above the left atrium 308.

According to an implementation, as represented in FIG. 4, a pacemaker 310 is shown with an arrangement of receivers. According to some embodiments, the pacemaker 310 (and 310' in FIG. 7) may be provided without the MEMS energy harvesting feature, while according to other embodiments, the energy harvesting feature, such as the MEMS, may be provided as part of the pacemaker. The receivers are arranged on the heart 300 to sense signals from activity (motion) occurring at or associated with the placed receiver position. According to an exemplary arrangement, the pacemaker 310 is arranged with a plurality of receivers, including a first receiver R1 associated with the left ventricle and provided at the left ventricle lateral wall or lateral-posterior wall 311, a second receiver R2 associated with the right ventricle 305 and provided at the inferior wall 312 of the right ventricle 305, a third receiver R3 associated with the left ventricle 306 and provided at the base of the heart at the inferior wall 313, a fourth receiver R4 associated with the right ventricle (RV) and being provided at the base of the heart at the inferior wall 314 of the right ventricle 305, and a fifth receiver R5 associated with the interventricular septum 304. The fifth receiver R5 preferably is positioned to the right of the interventricular artery 315, which according to some embodiments may be about 1 cm therefrom.

The receivers R3 and R4 preferably are disposed along the atrioventricular groove and are disposed under the vessels (e.g., about 1 cm lower than the vessels). As depicted in FIG. 4, a receiver R6 is provided at the right atrial appendage (RAA).

In FIG. 4, the receivers (e.g., such as those R1, . . . R6 in the arrangement depicted), preferably include mounting means for attaching a respective receiver (Rn) to a location of the heart 300. The mounting means is shown comprising a spiral element or wire that may be inserted into the heart. For example, the spiral element or wire 320 is shown attaching the receiver R4 to the heart 300. Preferably, the mounting element is inserted epicardially, and may be done with the use of a surgical instrument (e.g., such as a thoracoscope or other suitable instruments). The receivers (R1 . . . R5) preferably are located in the thickness of the myocardium, as shown by the wire elements of each receiver. According to preferred embodiments, the mounting element length is provided to be suitable to attach the respective receiver (Rn) to its desired location, and to insert, when installed, at a suitable or desired depth for sensing heart movements and delivering electrical impulses.

Figure 5:
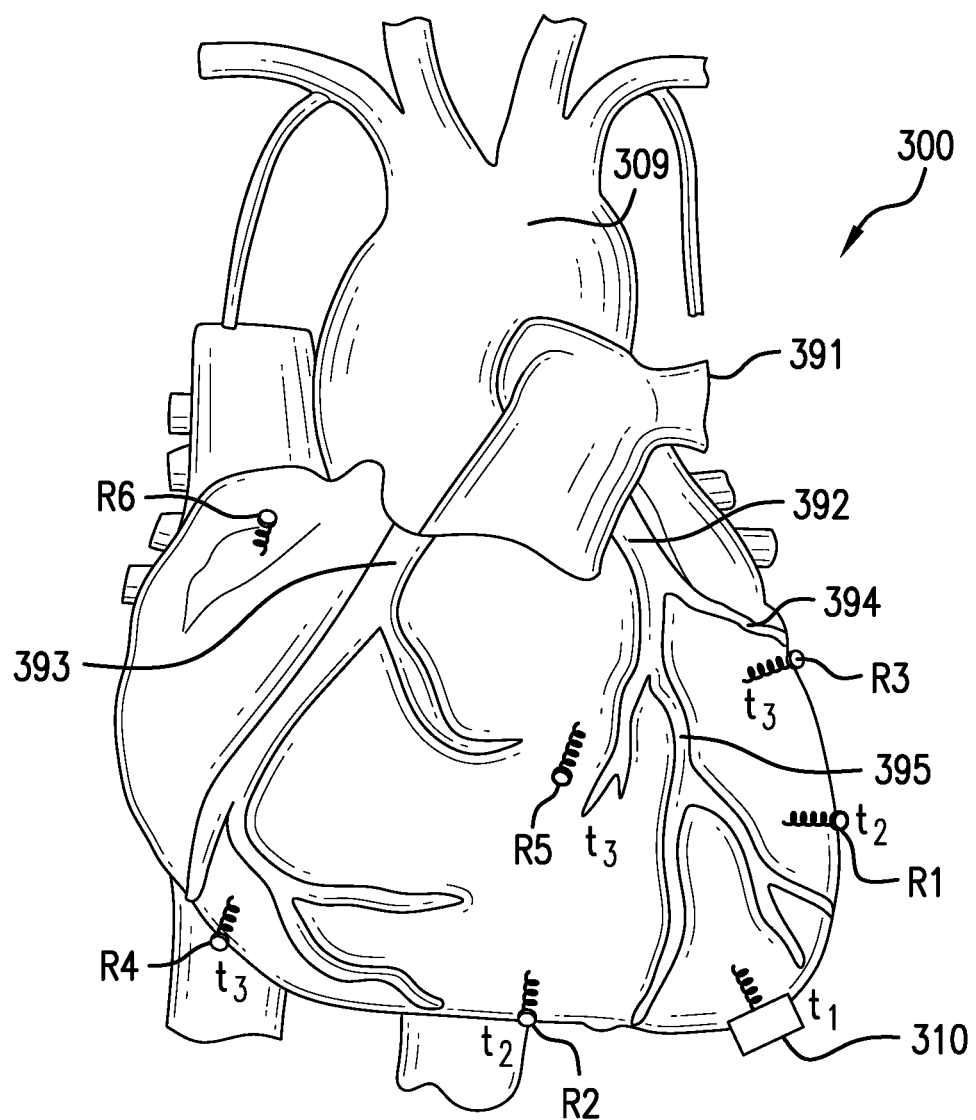
FIG. 5 is a schematic representation of the heart depicted in FIG. 4, showing the exterior surface and arteries.

FIG. 5 depicts the heart 300 and illustrates a preferred arrangement of the receivers (R1 . . . R5). The receivers (R1 . . . R5) are positioned on the surface of the heart 300, and extend into the myocardium. A pacemaker 310 is shown, and preferably communicates with the receivers to receive signals (electrical impulses corresponding to the heart activity at the corresponding receiver location), and to send signals to actuate the receiver to deliver an electrical impulse to the heart 300 at the receiver location.

Figure 6:
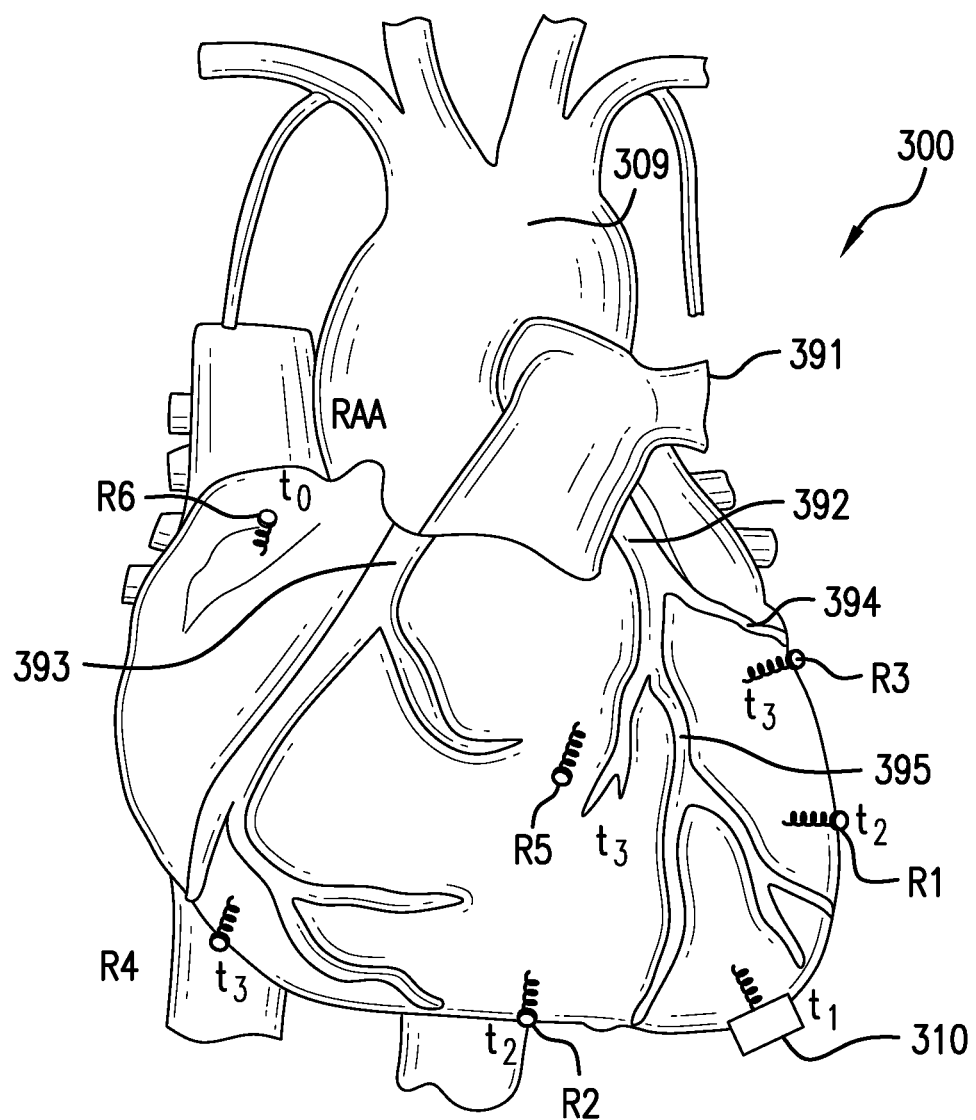
FIG. 6 is another schematic representation of the heart depicted in FIG. 5, showing the exterior surface and arteries, and showing the RAA receiver (right atrial appendage receiver).

FIG. 6 is similar to the depiction of FIG. 5, but further indicates the (right atrial appendage) RAA receiver, R6, shown disposed at the right atrial appendage. The receiver R6, preferably functions in a similar manner to the receivers (R1 . . . R5), and provides sensing and impulse delivery to the RAA.

Figure 7:
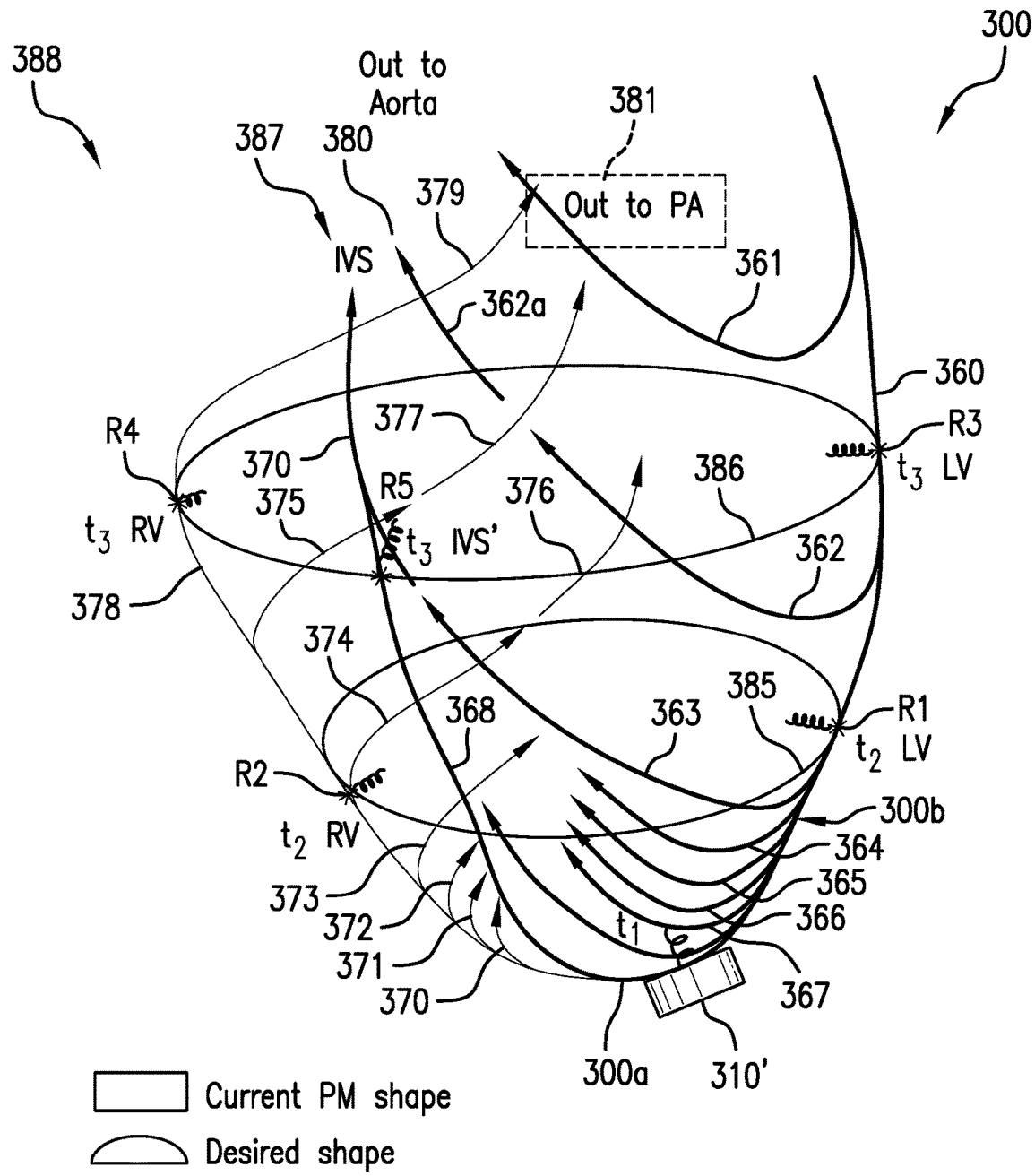
FIG. 7 is a schematic diagram of a heart, illustrating the left ventricle (LV)-right ventricle (RV) kinematics, in a multi-sensing pacing implementation.

FIG. 7 is a schematic diagram of the heart 300', illustrating the left ventricle (LV)-right ventricle (RV) kinematics. The left ventricle (LV) oblique fibers represented in the schematic by lines 360, 361, 362, 363, 364, 365, 366, 367, 368 and 370 are disposed toward the aorta 380. The right ventricle (RV) oblique fibers, represented in the schematic by lines 370, 371, 372, 373, 374, 375, 376, 377, 378 and 379 are disposed toward the pulmonary artery (PA) 381. The circumferential fibers, represented by the fibers 385, 386, are disposed predominantly in the middle of the right ventricle (RV)-left ventricle (LV) wall). The interventricular septum (IVS) 387 also is shown. The right atrial appendage (RAA) 388 also is shown in the diagram. An exemplary arrangement of the receivers (R1 . . . R5) is shown in connection with the fiber direction. The receivers preferably are configured to sense heart operation, and communicate a signal (a wireless signal in the arrangement depicted) to the pacemaker 310', shown positioned at the apex 300*a* of the heart 300 at the left ventricular side 300*b*. The pacemaker 310' receives the signals from the receivers and processes and analyzes the signals to determine the representative activity or condition of the heart 300. The analysis undertaken by the pacemaker circuitry also determines, based on settings and thresholds, whether and when to send a trigger for a receiver (Rn) to discharge an electrical impulse. The pacemaker 310' preferably may control the receivers to produce an order of discharges (whether consecutively, simultaneously, or combinations thereof), to direct the movement of the heart at particular locations. According to preferred implementations, the pacemaker processes the information, and delivers signals to the respective ones of the receivers (Rn), which in this example, are the receivers R1 . . . R5 (and optionally R6). The receivers (R1 . . . R5, (R6)) are actuated to replicate the operation of a normally functioning heart.

Figure 1:
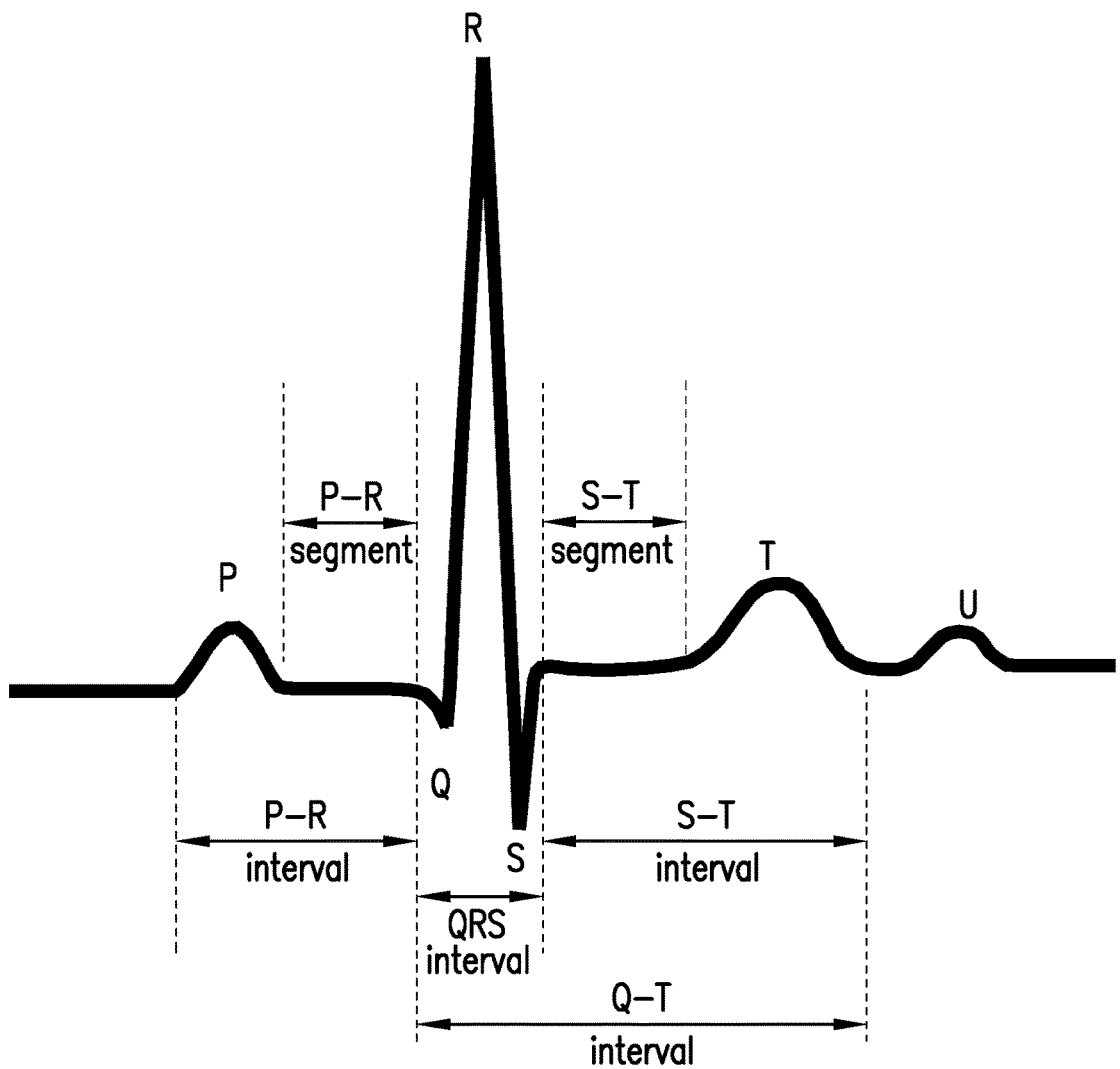
FIG. 1 is a depiction of an ECG signal representation showing a one-cycle ECG tracing for a normal healthy heart.

Referring again to FIGS. 5 and 6, the heart 300 is depicted with a plurality of the receivers R1 . . . R6 installed thereon. The heart 300 shows the exterior with the arteries represented thereon, including the aorta 309, the left internal mammary artery 391, the left main coronary artery 392, the right coronary artery 393, the circumflex coronary artery 394, and the left anterior descending coronary artery 395. The pacemaker 310 is shown installed at a position on the heart 300 (at the apex 300*a*), and is associated with a time value t1. The receivers R1 . . . R5 (and R6) are mounted on the epicardium, and are positioned in the locations represented by the receivers in FIG. 1. The receivers each represent a position on the heart and an associated time reference, as follows: R1:t2, R2:t2, R3:t3, R4:t3, R5:t3, and R6 (when present):t0. The time values are as follows:

t=time
RAA=t0 (time zero)
t1=time 1
t2=time 2
t3=time 3

According to preferred implementations, the timing sequencing may be carried out as follows, where: t1 is earlier than t2, and t2 is earlier than t3; or may be carried out where t1=t2=t3.

The sequencing preferably is carried out with the pacemaker circuitry, which may include one or more microcontroller, microprocessor, or microelectronic mechanical unit (MEMS), as well as combinations of these. The pacemaker circuitry is configured with software containing instructions that process the signals received from the receivers at the locations on the heart 300, and analyzes the heart activity, as reported from the receivers (locations). The pacemaker 310 paces the heart 300 at the desired locations to produce a replication of the normal heart movement, i.e., contractions. According to one example, the system preferably is operated by installing a plurality of receivers on the heart (e.g., R1 . . . R5/R6), each receiver being in communication with pacing circuitry (e.g., the pacemaker 310), wherein the pacing circuitry receives signals from the receivers that indicate a condition of the heart sensed at that respective receiver location, and wherein the pacing circuitry (e.g., the pacemaker 310) processes the signals from the receivers, and communicates an instruction to one or more of those receivers for the receiver to deliver an electrical impulse to the heart 300 at the location where the receiver is located. The pacing circuitry operates the receiver signal delivery at each receiver location to cause the plurality of receivers to deliver electrical signals to the heart at their respective locations, at a time to produce a normal contraction of the heart. The time sequencing is controlled with software containing instructions to monitor the signals communicated from the receivers which correspond to the heart activity, and to actuate the delivery of an electrical impulse at a location of the heart (where a receiver is located) to cause the heart to contract. The timing is carried out to produce a normal contraction of the heart by actuating the fibers (see FIG. 7).

Figure 8:
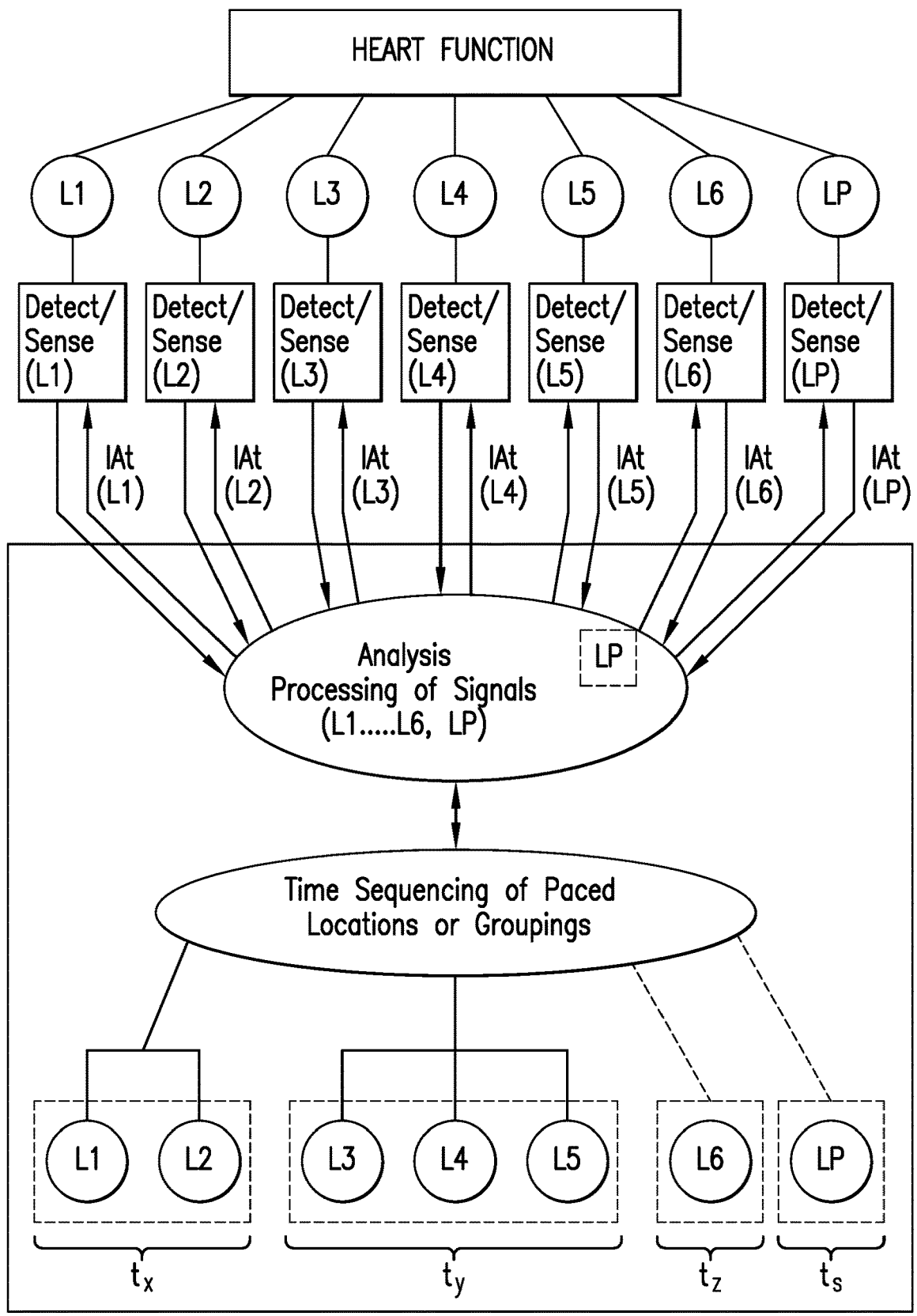
FIG. 8 is a flow diagram schematically illustrating the system and method for heart pacing using the multi-point pacing.

Referring to FIG. 8, a flow diagram schematically illustrates the system and method for heart pacing using the multi-point pacing shown and described herein. A plurality of locations are designated on the heart for positioning the receivers. The schematic diagram in FIG. 8 shows the receivers represented as detection and sensing functions, detect/sense, for each corresponding location. In FIG. 8, a plurality of locations (L1 . . . L6, as well as the pacemaker location (LP)), are depicted. There could be other numbers of pacing locations. The heart function is monitored at the designated locations (L1 . . . L6, and LP), and the signals corresponding to the sensed heart function (such as, for example, the presence of and/or level of heart activity, contractions, or absence thereof), is communicated to the pacing circuitry. Analysis and processing of the signals is carried out, so that each of the designated heart locations has a report of function (or lack thereof). The diagram in FIG. 8 also shows the time sequencing, which is preferably time sequencing of designated locations. The locations (L1 . . . L6, and LP) may be separate, or preferably may be grouped for time pacing of one or more of the locations (separately, or simultaneously). In FIG. 8, a grouped time sequencing is shown for two locations (L1 and L2), representing a first time sequencing group, and for a second grouping of locations (L3, L4, L5) representing the second time sequencing group. In this depiction, the third time sequencing is represented by a single location (L6), which is shown as an optional pacing location. In this depiction, a fourth time sequencing is represented by a pacemaker location (LP), which may be the location where the pacemaker is installed (preferably on the heart surface, or at the heart location to sense and deliver impulses at that location), providing another point for sensing and detecting. The time sequencing is carried out to deliver electrical impulses to the locations (L1 . . . L6, and LP), in accordance with the pacing scheme to be carried out. The illustration in FIG. 8 also shows the electrical impulse actuation at the designated pacing locations (L1, . . . L6, and LP). A series of connections are depicted (IAt), which are impulse actuations (IA), at a time t. For example, according to the groupings represented by FIG. 8, IAt(L1), and IAt(L2), it is shown that electrical impulses are delivered simultaneously at locations L1 and L2, at a time tx. Locations L3, L4 and L5, receive electrical impulse actuation together at time interval ty. In the depiction, IAt(L6) would receive an electrical impulse at a time tz.

According to some embodiments, the electrical impulse delivery is dependent upon the signal detection, and the processing of activity. Where the signals indicate normal function, the pacing delivery of electrical impulses to the corresponding location may be withheld, while when signals indicate a lack of activity or abnormal operation, the electrical impulse may be delivered.

The sequential pacing may be carried out in response to events sensed and detected by the signals provided by the receivers at locations on the heart, as well as the pacemaker (and its location). The pacemaker circuitry for example, may include circuitry, which preferably includes one or more chips, micro schema, microprocessors or microcontrollers, and/or MEMS, that receive the signals from the receivers and which can store and/or process the signals to determine timing intervals for the signal activity represented. For example, the signal represents the heart activity, such as, for example, a contraction. The signal may be processed to determine whether it meets a threshold, and a plurality of signals from different receivers (and/or the pacemaker—which may also function as a receiver, e.g., self-contained) may be processed to determine whether a threshold is met, and to analyze timing intervals between one or more signals from the one or more respective locations. The timing signals, as well as the signal strength, timing, and patterns, for a given signal, plurality of signals, or one or more signals, or comparisons, preferably are analyzed to determine whether the heart activity is normal. If an event is detected indicating a heart activity condition that requires correction or an adjustment, the pacing circuitry determines the needed correction or adjustment to be made to bring the heart activity into conformance with the designated normal function for the patient or such heart activity. The pacing circuitry then responds by generating a signal for the delivery of one or more electrical impulses at the locations where the adjustment or correction is needed. Preferably, the pacing circuitry delivers the signal to actuate delivery of an impulse at the receiver location, which may involve one or more receivers and the timing of the signal impulse delivery. The pacing circuitry may deliver sequentially arranged or programmed impulses to a sequence of locations of the heart, through the respectively located receivers positioned on the heart. The pacing circuitry may be programmed or programmable to address heart conditions, and provide remedial relief through the pacing, which may include sequential, concurrent, or combinations thereof at the receiver (and pacemaker locations). Alternatively, the receivers may be configured to sequentially or concurrently pace one or more receivers or groups, and deliver impulses based on sensed activity at one or more heart locations (preferably receiver locations). Alternatively, the receivers may be programmed to deliver impulses based on a time sequence or time interval.

In the above embodiments, in addition, or as an option, the MEMS unit may be provided in conjunction with the pacemaker circuitry to harvest kinetic energy from the heart movements (e.g., contractions), and convert the kinetic energy to electrical energy to power the pacemaker functions, and/or for providing power or charging a battery. Movement of the device is effected through the kinematic motion of the heart (e.g., heart beats). The pacing circuitry may include or be coupled with a microelectronic mechanical unit or component, such as a MEMS, that converts the heart motion into electrical energy. In the embodiments disclosed and described herein, pacing circuitry may be powered by a battery which preferably is provided in or as part of the pacemaker casing, and which is coupled to the pacing circuitry.

While the invention is described through the above-described exemplary embodiments, it will be understood by those of ordinary skill in the art that modifications to, and variations of, the illustrated embodiments may be made without departing from the inventive concepts disclosed herein. For example, although some aspects of the system and method have been described with reference to a flowchart, those skilled in the art should readily appreciate that functions, operations, decisions, etc. of all or a portion of each block, or a combination of blocks, of the flowchart may be combined, separated into separate operations or performed in other orders. In addition, although preferred embodiments of a pacemaker are illustrated in exemplary embodiments, the multi-point pacing system may be applied for use with other pacemakers (e.g., other leadless pacemakers). For example, according to some embodiments, pacemakers and/or pacing circuitry may be provided without an energy harvesting feature (such as a MEMS), while according to other embodiments, the energy harvesting feature, such as the MEMS, may be provided as part of the pacemaker or pacing circuitry. For example, according to some embodiments, pacemakers and/or pacing circuitry may be provided without an energy harvesting feature (such as a MEMS), while according to other embodiments, the energy harvesting feature, such as the MEMS, may be provided as part of the pacemaker or pacing circuitry. Alternatively, the devices of shown and described may be used to treat the heart of an individual, such as, for example, in children, where a receiver may be placed on the atrium, so that there is a pacemaker and t0 (or RAA) only, such as the pacemaker (PM 310) of FIG. 4, and the receiver R6 (at the RAA) at t0, this arrangement being useful for treating heart conditions using left ventricle LV pacing. For example, since the receiver will be positioned on the surface of the heart at the RAA, a small incision (1 to 2 cm) may be used with thoracoscopy techniques to implant the receiver (E.g., R6 at the RAA). The pacemaker (such as the pacemaker 310 of FIG. 4), may be implanted on the heart at the apex, using any of the techniques discussed herein or other conventional techniques. A plurality of receivers are shown being provided on the heart surface. Preferably, the receivers also contain an electrode that is inserted into the myocardium. Suitable methods for implanting the receivers include thoracoscopy, where for example, two or three small holes may be made through the skin surface into the cavity where the heart is located. For example, a suitable method involves one hole for the suture and scissors instrument, another for the forceps, and another for a camera and/or light. The lumens may be inserted through the openings or holes, and the instrumentation passed through the lumens, or instrumentation that has integral lumens may be used. The receiver may be held with a forceps or other suitable holder, and moves through the lumen to the implantation site. The instruments then are used to rotate the receiver to implant the spiral electrode into the myocardium, with the receiver remaining at the surface of the heart. The same openings may be used to implant a number of different receivers at different locations on the heart, or in other cases, sets of openings may be made, or one or more additional openings made. The invention provides for receivers to be positioned and operated an multiple sites of the heart. For example, the system may be sued to treat patients with large ventricles, where multi-site pacing at locations that will produce in the ventricles, the desired spiral movement, can be effected with the receivers and their locations to restore spiral movement continuously to the heart. According to some embodiments, the devices and system may be used to effect a synchronization of the heart so that the heart operation to synchronize the LV and RV operations so that the bold filling and ejection is carried out in accordance to promote complete filling of the ventricle to reduce the mitral regurgitation volume. The system and devices may be applied to the heart and operated to reduce or eliminate conditions where (in the diastolic condition) the LV is still filling with blood (e.g., because it is large) while the RV starts to contract. The system and devices may be applied and operated to permit the LV to more completely fill and synchronize with the operation of the RV. For example, the devices may be located on the heart and operated to effect a spiral movement via induced contractions from the electrical impulses delivered from the receivers. The implementation may be used to control the filling operation and ejection operations, so that contraction is controlled to allow filling (as in the LV) and not push the flow out thereof until desired. A suitable monitoring procedure may be carried out during the implantation of the devices (e.g., the receivers and pacemakers) to evaluate the desired positioning for implanting the receivers. For example, one may monitor the procedure, and the injection fraction using echocardiography, to provide positioning of the receiver to produce a desired effect (stimulation of the heart). For example, the receivers may be positioned around the heart to create an electrical loop, so as to produce stimulation at locations that will stimulate the locations. For example, during implantation the receivers may be located to avoid potential fibrotic areas (where electrical conductivity may be limited, or where it may be diffuse or dispersive and detoured from the desired location, and not produce the stimulation at the desired location). The receivers are programmed or reprogrammed to pace at the same pace or consecutively, or in other arrangements (in one or more groups). Receivers may be positioned to address conditions where there is fibrosis or other impediment present, that stops or detours the electrical transmission (for example, where a heart is large, and there is fibrotic tissue). Suitable radio frequencies may be generated by the pacing circuitry or pacemaker to operate the receivers.

Embodiments of the devices and system may implement an energy harvesting feature from the kinematic motion of the heart. The energy harvesting feature may be positioned in the pacemaker unit in conjunction with pacing circuitry. Exemplary components for harvesting the energy may include a piezoelectric material configured in a harvesting circuit to provide power or charging. The electrical charge accumulating may be induced in the piezoelectric material due to mechanical deformations of the material, which may be produced by the movement of the heart. Embodiments of the invention show and describe receivers. Receivers used to carry out the methods disclosed herein may be suitable receivers that are configured to deliver electrical impulse to the heart, and which include wireless communication capability, and may power their functions using acoustic or RF energy. For example, receivers may be powered by an associated pacemaker that is configured to produce acoustic or RF energy which the receiver circuitry may convert to usable energy to power the receive functions. According to some embodiments, the receiver may be similar to or may be commercially obtained. According to preferred embodiments, receivers are powered using a wireless power source, such as acoustic or RF waves (which may be generated by a proximally located generating source, such as a pacemaker). According to some other embodiments, the methods and systems may be carried out where one or more receivers includes a power source, such as a battery. Receivers preferably also include the capability to receive programming instructions, such as to receive, identify and respond to a trigger or actuation signal from the pacemaker pacing circuitry, and preferably also to deliver information detected by the receiver sensing functionality to the pacemaker (e.g., pacing circuitry). In addition, although depicted as circular in the exemplary embodiments, the multi-part pacemakers may have other configurations, including for example, the pyramidal shaped or a shape with rounded edges or corners, or other suitable shapes. In addition, while the pacemaker parts are depicted to illustrate alternate connections of the electrode and case circuitry, a connection mechanism shown in one depiction may be applied for use in another of the illustrated embodiments. Further while the case circuitry of the pacemakers, including the multi-part pacemakers, is represented schematically in the figures using boxes and/or lines, the circuitry may include a single circuit component, or may comprise multiple components, connected circuits, power supplies, communications components, transceivers, antennas, RF generators, and the like.

Furthermore, disclosed aspects, or portions of these aspects, may be combined in ways not listed above. Accordingly, the invention should not be viewed as being limited to the disclosed embodiments. The description is illustrative and is not to be construed as limiting the scope of the invention. Various modifications and changes may occur to those skilled in the art without departing from the spirit and scope of the invention described herein, and as defined by the appended claims.

What is claimed is:

1. A system for monitoring and treating conditions of a mammalian heart, comprising:
 a) an epicardial pacemaker having:
  i) a case;
  ii) electrical circuitry sealed within the case;
  iii) an electrode having a tip and being electrically coupled to the electrical circuitry;
 b) wherein the electrical circuitry of the pacemaker is configured to provide one or more functions to treat one or more conditions of the heart; and
 c) epicardial receivers that detect and relay electrical signals from the heart corresponding to the operation of the heart;
 d) wherein said receivers and said pacemaker communicate wirelessly with each other; and
 e) wherein said pacemaker and said receivers are implantable;
 f) wherein said receivers include at least one first receiver R1 configured for operation at a first location at the left ventricle to electrically stimulate the oblique fibers of the left ventricle, and at least one second receiver R2 configured for operation at a second location at the right ventricle to electrically stimulate the oblique fibers of the right ventricle, and a third receiver R3 configured for operation at a third location at the left ventricle to electrically stimulate the oblique fibers of the left ventricle, and at least one additional receiver R5 configured for operation at the interventricular septum, and at least one other additional receiver R6 configured for operation at the right atrial appendage; and
 g) wherein the circuitry is configured to operate each receiver to deliver electronic impulses from each respective receiver, in a sequence that delivers electronic impulses from the respective receivers to produce spiral contraction of the oblique fibers so that at an initial time t0, the receiver R6 at the right atrial appendage provides the initial stimulation of the right atrial appendage, which continues to the left atrium, and so that thereafter at time t1, the pacemaker provides stimulation at the apex, and so that thereafter, at time t2 the respective receivers nearest to the apex of the heart, R1 and R2, provide electronic stimulation to both the right ventricle and left ventricle prior to time t3 when the receivers farther from the apex, R3 and R5, provide stimulation to both the left ventricle and interventricular septum.

2. The system of claim 1, wherein the electrical circuitry of the pacemaker is configured to group at least some receivers to provide group time sequencing of said at least some receivers.

3. The system of claim 2, wherein the electrical circuitry of the pacemaker is configured to group at least some of said receivers into at least two receiver groups to provide group time sequencing of the receivers in each of said at least two receiver groups, with each said receiver group having at least two or more receivers in said receiver group.

4. The system of claim 3, wherein each said receiver of a respective said receiver group is operated so that receivers in the said receiver group deliver electrical impulses together.

5. The system of claim 1, wherein said pacemaker comprises a multi-part pacemaker, including at least one first part and at least one second part, said first part including an electrode and at least another portion configured for contact with the heart epicardial surface, said electrode having a first end for implantation in a mammalian heart, and a second end; said second part including a case and circuitry sealed within said case, said second part being connectable to said first part, and wherein said first part electrode second end is configured to connect with said second part case circuitry.

6. The system of claim 1, wherein said pacemaker comprises a multi-part pacemaker, including at least one first part and at least one second part, said first part including an electrode that is implantable in a mammalian heart separate from said second part and at least another portion configured for contact with the heart epicardial surface, said second part including a case and circuitry sealed within said case, wherein said second part is separately implantable to connect with said first part when said first part is implanted in said mammalian heart.

7. The system of claim 1, wherein each receiver has an implantable electrode configured for epicardial implantation.

8. The system of claim 7, wherein said receiver electrodes are provided having at least two different lengths, so that at least one or more of said receivers has an electrode of a first length and at least one or more other said receivers has an electrode of a second length, wherein the second length is different than the first length.

9. The system of claim 1, wherein said pacemaker comprises circuitry that processes sensing signals received from the respective receivers and communicates actuation signals to one or more of said receivers to cause the one or more said receivers to deliver an electrical impulse.

10. The system of claim 9, wherein said pacing circuitry is configured with instructions to process said sensing signals and determine which of the respective one or more receiver locations corresponding with said one or more receivers requires pacing through delivery of an electrical impulse from a said receiver at a corresponding receiver location.

11. The system of claim 1, wherein said pacemaker circuitry includes one or more chips, micro schema, microprocessors or microcontrollers, and/or MEMS, that receive sensing signals from the receivers and store and/or process the sensing signals to determine timing intervals for the activity detected by the sensors and for pacing via the said receivers.

12. The system of claim 1, wherein said pacemaker has receiving and sensing functionality to sense activity signals, and to control delivery of electrical impulses.

13. The system of claim 1, including a MEMS that is configured to harvest energy from the heart.

14. The system of claim 1, wherein the receivers are configured to deliver an electrical impulse to the heart.

15. The system of claim 14, wherein the receivers are configured to deliver electrical impulses to the heart to pace the myocardium consecutively, from the apex toward the base of the heart.

16. The system of claim 14, wherein the system includes one or more receivers and at least one pacemaker, wherein each of said one or more receivers and said at least one pacemaker has an implantable electrode configured for epicardial implantation, and are further configured to deliver electrical impulses from said one or more receivers and said at least one pacemaker to replicate the operation of a normally functioning heart.

17. The system of claim 14, wherein each receiver is wirelessly powered via circuitry that converts RF or acoustic energy into electrical energy.

18. The system of claim 17, wherein each receiver includes a capacitor.

19. A method for treating one or more conditions of a mammalian heart, comprising:
   a) configuring a pacemaker to deliver electrical impulses to a heart;
   b) implanting the pacemaker at a location to deliver electrical impulses to the heart, said pacemaker having pacing circuitry;
   c) implanting a plurality of receivers at a respective plurality of locations on the heart to be monitored and regulated via the delivery of electrical impulses to those respective plurality of locations;
   d) monitoring the heart activity at the respective locations via said receivers;
   e) communicating activity signals from said receivers to said pacing circuitry, wherein said activity signals correspond to the heart activity monitored at said respective locations;
   f) monitoring the respective activity signals communicated from each said receiver that corresponds to the heart activity at the said respective receiver location;
   g) processing with said pacemaker pacing circuitry, said activity signals communicated from each said receiver,
   h) communicating an actuation signal from said pacemaker to one or more of the said receivers of the said plurality of receivers, and
   i) delivering an electrical impulse at one or more respective locations of the heart where the said respective receiver is located;
   j) wherein said receivers include at least one first receiver R1 configured for operation at a first location at the left ventricle to electrically stimulate the oblique fibers of the left ventricle, and at least one second receiver R2 configured for operation at a second location at the right ventricle to electrically stimulate the oblique fibers of the right ventricle, and a third receiver R3 configured for operation at a third location at the left ventricle to electrically stimulate the oblique fibers of the left ventricle, and at least one additional receiver R5 configured for operation at the interventricular septum, and at least one other additional receiver R6 configured for operation at the right atrial appendage; and
   k) wherein the circuitry is configured to operate each receiver to deliver electronic impulses from each respective receiver, in a sequence that delivers electronic impulses from the respective receivers to produce spiral contraction of the oblique fibers so that at an initial time to, the receiver R6 at the right atrial appendage provides the initial stimulation of the right atrial appendage, which continues to the left atrium, and so that thereafter at time t1, the pacemaker provides stimulation at the apex, and so that thereafter, at time t2 the respective receivers nearest to the apex of the heart, R1 and R2, provide electronic stimulation to both the right ventricle and left ventricle prior to time t3 when the receivers farther from the apex, R3 and R5 provide stimulation to both the left ventricle and interventricular septum.

20. The method of claim 19, wherein communicating activity signals from said receivers to said pacing circuitry, and wherein communicating an actuation signal from said pacemaker to one or more of the said receivers of the said plurality of receivers, comprise wireless communications.

\* \* \* \* \*